US010596125B2

(12) United States Patent
Desai et al.

(10) Patent No.: US 10,596,125 B2
(45) Date of Patent: Mar. 24, 2020

(54) NANOWIRE-COATED MICRODEVICE AND METHOD OF MAKING AND USING THE SAME

(71) Applicant: The Regents of the University of California, Oakland, CA (US)

(72) Inventors: Tejal A. Desai, San Francisco, CA (US); Hariharasudhan Chirra Dinakar, San Francisco, CA (US); Cade B. Fox, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 39 days.

(21) Appl. No.: 15/536,071

(22) PCT Filed: Dec. 11, 2015

(86) PCT No.: PCT/US2015/065360
§ 371 (c)(1),
(2) Date: Jun. 14, 2017

(87) PCT Pub. No.: WO2016/100136
PCT Pub. Date: Jun. 23, 2016

(65) Prior Publication Data
US 2017/0360717 A1    Dec. 21, 2017

Related U.S. Application Data

(60) Provisional application No. 62/092,125, filed on Dec. 15, 2014.

(51) Int. Cl.
*A61K 9/70*    (2006.01)
*A61L 31/16*    (2006.01)
(Continued)

(52) U.S. Cl.
CPC ............. *A61K 9/70* (2013.01); *A61K 9/7007* (2013.01); *A61K 47/32* (2013.01); *A61K 47/34* (2013.01);
(Continued)

(58) Field of Classification Search
CPC ...................................................... A61K 9/70
See application file for complete search history.

(56) References Cited

U.S. PATENT DOCUMENTS

| 5,567,271 A | 10/1996 | Chu et al. |
| 6,669,807 B2 | 12/2003 | Nakatani |

(Continued)

FOREIGN PATENT DOCUMENTS

| WO | 2005/033685 | 4/2005 |
| WO | 2008/109886 | 9/2008 |

(Continued)

OTHER PUBLICATIONS

Dougherty et al. Core-shell polymer nanorods by a two-step template wetting process. Nanotechnology 20 (2009) pp. 1-7 (Year: 2009).*

(Continued)

*Primary Examiner* — Cachet I Proctor
(74) *Attorney, Agent, or Firm* — Edward J. Baba; Shweta Chandra; Bozicevic, Field & Francis LLP

(57) ABSTRACT

A microdevice containing a plurality of nanowires on a biocompatible surface, and methods of making and using the same are provided. Aspects of the present disclosure include forming a plurality of microdevices on a substrate where each microdevice includes a plurality of nanowires. The nanowires may be loaded with an active agent by disposing the active agent onto the surface of the nanowires. Also provided herein are kits that include the subject microdevices.

18 Claims, 18 Drawing Sheets

(51) Int. Cl.
*A61K 47/32* (2006.01)
*A61K 47/34* (2017.01)
*A61M 37/00* (2006.01)
*B81B 7/00* (2006.01)
B82Y 30/00 (2011.01)
*A61K 9/00* (2006.01)

(52) U.S. Cl.
CPC ............ *A61L 31/16* (2013.01); *A61M 37/00* (2013.01); *B81B 7/00* (2013.01); *A61K 9/0097* (2013.01); *A61L 2400/12* (2013.01); *B82Y 30/00* (2013.01)

(56) References Cited

U.S. PATENT DOCUMENTS

| | | | |
|---|---|---|---|
| 7,393,391 B2 | 7/2008 | Lopez et al. | |
| 2005/0221072 A1* | 10/2005 | Dubrow | A61F 2/30767 428/292.1 |
| 2005/0266067 A1 | 12/2005 | Sengupta et al. | |
| 2007/0082393 A1* | 4/2007 | Lodhi | A61L 27/38 435/325 |
| 2009/0214474 A1 | 8/2009 | Jennings | |
| 2010/0055154 A1* | 3/2010 | Liao | A61K 9/0092 424/443 |
| 2010/0278720 A1* | 11/2010 | Wong | B01J 23/06 423/604 |
| 2010/0303881 A1* | 12/2010 | Hoke | A61K 9/70 424/423 |
| 2010/0318193 A1* | 12/2010 | Desai | A61L 27/04 623/23.76 |
| 2013/0216779 A1* | 8/2013 | Hofmeister | G03F 7/0002 428/141 |
| 2014/0170204 A1 | 6/2014 | Desai et al. | |
| 2014/0234381 A1* | 8/2014 | Tao | A61L 27/18 424/400 |

FOREIGN PATENT DOCUMENTS

| WO | 2012/1102678 | 8/2012 |
|---|---|---|
| WO | 2012/1135065 | 10/2012 |

OTHER PUBLICATIONS

Fan et al. (2003) "Fabrication of Silica Nanotube Arrays from Vertical Silicon Nanowire Templates" J. Am. Chem. Soc. 125(18): 5254-5255.

Fine et al. (2013) "Silicon Micro- and Nanofabrication for Medicine" Adv. Healthcare Mater. 2: 632-666.

Du and Gan (2012) "Cellular Interactions on Hierarchical Poly([epsilon]-caprolactone) Nanowire Micropatterns" ACS Applied Materials & Interfaces 4(9): 4643-4650.

Uskokovic et al. (2012) "Shape Effect in the Design of Nanowire-Coated Microparticles as Transepithelial Drug Delivery Devices" ACS Nano 6(9): 7832-7841.

* cited by examiner

NANOWIRE-COATED MICRODEVICE AND METHOD OF MAKING AND USING THE SAME

CROSS-REFERENCE TO RELATED APPLICATION

This application is based upon and claims priority to U.S. provisional patent application 62/092,125, filed Dec. 15, 2015, which is incorporated herein by reference in its entirety.

INTRODUCTION

Substrates that contain micro- and nanoscale features are important for a number of biological applications. Because micro- and nanotopography influence cellular adhesion, alignment, shape, proliferation, and differentiation, topographical cues incorporated into cellular scaffolds are capable of controlling a wide range of cellular behaviors. Hierarchical structures provide enhanced control, as cells are influenced both on the microscale by contact guidance and on the nanoscale through direct interaction of cellular receptors with external physical cues. Hierarchical substrates may also have utility for micron-scale reagent and drug loading of miniaturized biological assays and biomedical microdevices.

SUMMARY

A microdevice containing a plurality of nanowires on a biocompatible surface, and methods of making and using the same are provided. The microdevice facilitates efficient loading of a therapeutic agent onto the surface of the nanowires which provide for loading of the therapeutic agent via capillary action. The increased surface area of the microdevice also enables loading of a greater amount of the therapeutic agent.

Aspects of the present disclosure include a method of forming a plurality of nanowires on a biocompatible surface, including the steps of depositing a second biocompatible polymeric layer onto a surface of a first biocompatible polymeric layer, contacting a nanoporous membrane with a surface of the second biocompatible polymeric layer, and forming a plurality of nanowires from the second biocompatible polymeric layer using the nanoporous membrane as a template.

In any method embodiment of forming a plurality of nanowires on a biocompatible surface set out above or infra, the contacting step may include contacting the nanoporous membrane with the second biocompatible polymeric layer under heat.

In any method embodiment of forming a plurality of nanowires on a biocompatible surface set out above or infra, the forming step may include dissolving the nanoporous membrane. In certain embodiments, the dissolving may include etching the nanoporous membrane in an alkaline solution.

In any method embodiment of forming a plurality of nanowires on a biocompatible surface set out above or infra, the depositing step may include contacting a heated first biocompatible polymeric layer with the second biocompatible polymeric layer.

In any method embodiment of forming a plurality of nanowires on a biocompatible surface set out above or infra, the first biocompatible polymeric layer may include a biocompatible polymer selected from the group consisting of: polymethyl methacrylate (PMMA), collagen, poly(lactic acid) (PLA), polyglycolic acid (PGA), poly(anhydrides), poly(hydroxy acids), poly(lactic-co-glycolic acid) (PLGA), chitosan PEG or PEGDMA, or combinations thereof.

In any method embodiment of forming a plurality of nanowires on a biocompatible surface set out above or infra, the second biocompatible polymeric layer comprises a biocompatible polymer selected from the group consisting of: polycaprolactone (PCL), gelatin, agarose, poly(anhydrides), poly(hydroxy acids), poly(propylfumerates), poly(lactic-co-glycolic acid) (PLGA), chitosan, or combinations thereof.

In any method embodiment of forming a plurality of nanowires on a biocompatible surface set out above or infra, the nanoporous membrane may be an anodized metal oxide membrane or a nanoporous silica membrane. In certain embodiments, the anodized metal oxide may contain aluminum, tin or titanium. In certain embodiments, the nanoporous membrane is a nanoporous anodized aluminum oxide (AAO) membrane.

In any method embodiment of forming a plurality of nanowires on a biocompatible surface set out above or infra, the method may include creating a micropattern in the first biocompatible polymeric layer prior to depositing the second biocompatible polymeric layer onto a surface of the first biocompatible polymeric layer. In certain embodiments, creating a micropattern includes using photolithography.

In any method embodiment of forming a plurality of nanowires on a biocompatible surface set out above or infra, the method may include creating a micropattern in the nanoporous membrane prior to contacting a nanoporous membrane with a surface of the second biocompatible polymeric layer. In certain embodiments, creating a micropattern includes using photolithography.

In any method embodiment of forming a plurality of nanowires on a biocompatible surface set out above or infra, the method includes providing the first biocompatible polymeric layer on a substrate. In certain embodiments, the substrate is a silicon wafer.

In any method embodiment of forming a plurality of nanowires on a biocompatible surface set out above or infra, the first polymeric layer has an average thickness in the range of 1 to 100 µm.

In any method embodiment of forming a plurality of nanowires on a biocompatible surface set out above or infra, the second biocompatible polymeric layer has an average thickness in the range of 1 to 100 µm.

In any method embodiment of forming a plurality of nanowires on a biocompatible surface set out above or infra, the average diameter of the pores of the nanoporous membrane is in the range of 10 to 500 nm.

Further aspects of the present disclosure include a microdevice containing a plurality of nanowires disposed on a biocompatible surface, wherein the microdevice is formed by a process including any method embodiment of forming a plurality of nanowires on a biocompatible surface set out above.

In any microdevice embodiment set out above or infra, the first and second biocompatible polymeric layers comprise a micropattern. In certain embodiments, the microdevice is disposed on a substrate.

In any microdevice embodiment set out above or infra, the nanowires have an average diameter of 10 to 500 nm.

In any microdevice embodiment set out above or infra, the nanowires have an average length of 1 to 100 µm.

In any microdevice embodiment set out above or infra, the microdevice includes an active agent disposed on the plurality of nanowires.

Also provided herein is a method of loading a microdevice containing a plurality of nanowires on a biocompatible surface with an active agent, the method including contacting a microdevice of any of the microdevice embodiments set out above with a solution that contains an active agent, thereby loading the microdevice containing a plurality of nanowires on a biocompatible surface with an active agent.

In any method embodiment of loading a microdevice containing a plurality of nanowires on a biocompatible surface with an active agent set out above or infra, the method includes drying the microdevice. In some embodiments, the drying includes inverting the microdevice such that the biocompatible surface containing the nanowires substantially faces down.

Also provided herein is a method of delivering an active agent to a mucosal surface, the method including contacting a plurality of nanowires of a microdevice that contains the plurality of nanowires on a biocompatible surface with a mucosal surface, wherein an active agent is disposed on the plurality of nanowires.

DETAILED DESCRIPTION

Figure 1:
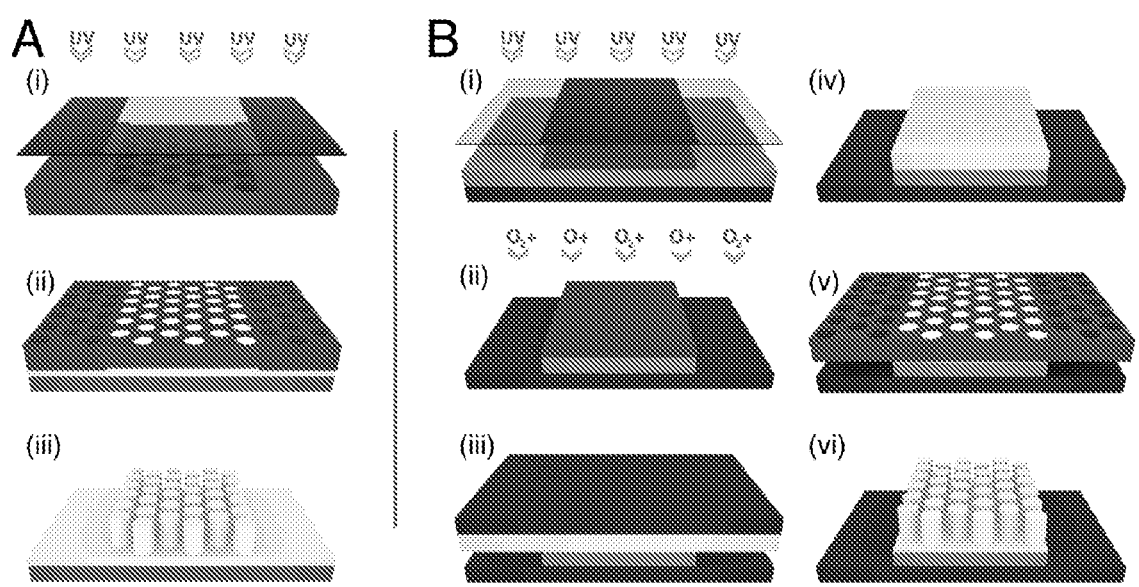
FIG. 1 shows a schematic of an exemplary method for fabricating nanowire-coated microdevices, according to embodiments of the present disclosure.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a microdevice" includes a plurality of such microdevices and reference to "the active agent" includes reference to one or more active agents and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Method of Forming a Microscale Device with Plurality of Nanowires

Microdevices containing a plurality of nanowires on a biocompatible surface, and methods of making and using the same are provided. Aspects of the present disclosure includes a method of forming a plurality of nanowires on a biocompatible surface, e.g., in a microdevice. The subject microdevices include a plurality of nanowires disposed on a biocompatible surface, wherein the biocompatible surface includes a first biocompatible polymeric layer and a plurality of nanowires formed from a second biocompatible polymeric layer disposed on a surface of the first biocompatible polymeric layer. The microdevices containing a plurality of nanowires disposed on a biocompatible surface find use in loading active agents on the plurality of nanowires for delivery of the active agents to a mucosal surface in a subject in need of treatment. Further aspects of the present disclosure are described in detail below.

Disposing a Second Biocompatible Polymer Layer onto a First Biocompatible Polymer Layer As summarized above, aspects of the present disclosure include a method of forming a plurality of nanowires on a biocompatible surface, e.g., a biocompatible surface of a microdevice. The biocompatible surface may be a surface of a layer of a biocompatible polymer, i.e., a biocompatible polymer membrane. In certain embodiments, the biocompatible polymer layer is substantially planar. In certain embodiments, the plurality of nanowires is formed by molding at least part of the biocompatible polymer layer, using a nanoporous membrane as the template. Thus, in certain embodiments, the subject method of forming a plurality of nanowires on a biocompatible surface produces a microdevice that includes a biocompatible polymeric substrate wherein a first surface of the biocompatible polymeric substrate is substantially flat and a plurality of nanowires is disposed on a second surface of the biocompatible polymeric substrate, opposite the first surface, by molding at least part of the biocompatible polymer substrate using a nanoporous membrane as a template.

Figure 9:
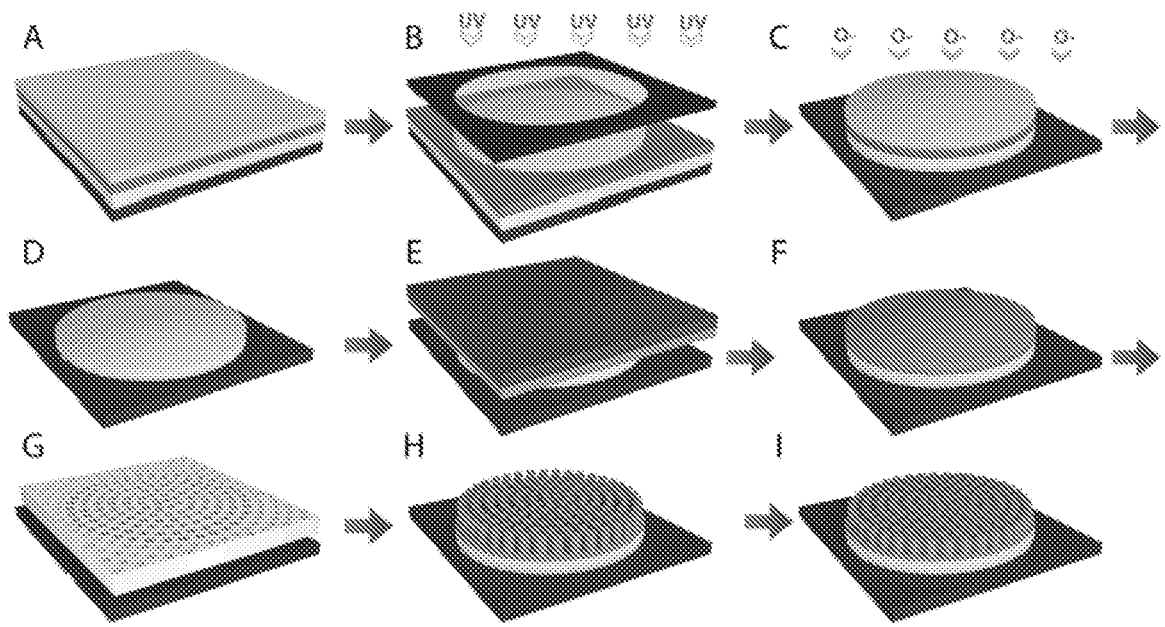
FIG. 9 shows another schematic of a method for fabricating a nanowire-coated microdevices, according to embodiments of the present disclosure.
Figure 10:
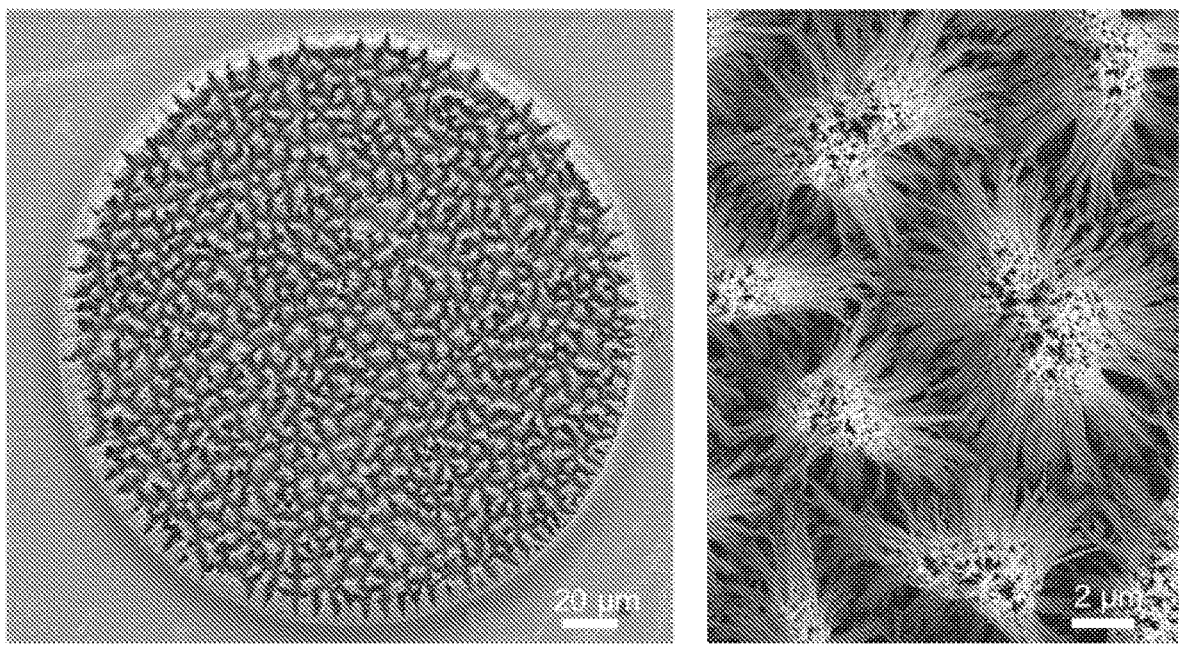
FIG. 10 shows SEM micrographs of a nanowire-coated microdevice, according to embodiments of the present disclosure.

A method of forming plurality of nanowires on a biocompatible surface includes depositing a second biocompatible polymeric layer onto a surface of a first biocompatible polymeric layer (see, for examples, FIGS. 1 and 9). In certain embodiments, the first biocompatible polymeric layer may be provided on a substrate, including, but not limited to, a silicon wafer. The first biocompatible polymeric layer may be deposited on the substrate using any convenient method. In certain embodiments, the first biocompatible polymeric layer is deposited onto a substrate by spin-coating.

The second biocompatible polymeric layer may be deposited onto the first biocompatible polymeric layer in any suitable manner. In certain embodiments, the second biocompatible polymeric layer is deposited onto the first biocompatible polymeric layer such that the second biocompatible polymeric layer covers substantially the entire area of a surface of the first biocompatible polymeric layer. In certain embodiments, the second biocompatible polymeric layer coats substantially the entire area of a surface of the first biocompatible polymeric layer.

The second biocompatible polymeric layer may be deposited onto the first biocompatible polymeric layer using any suitable method. In certain embodiments, the second biocompatible polymeric layer is deposited onto the first biocompatible polymeric layer by spin-coating.

In another embodiment, the second biocompatible polymeric layer is deposited onto the first biocompatible polymeric layer by heating the first biocompatible polymeric layer and contacting the heated first biocompatible polymeric layer with the second biocompatible polymeric layer. In some cases, the first biocompatible polymeric layer is provided on a substrate, such as, but not limited to, a silicon wafer. In certain embodiments, the first biocompatible polymeric layer is heated to a temperature above the melting temperature of the second biocompatible polymeric layer, thereby bonding the first biocompatible polymeric layer with the second biocompatible polymeric layer. In certain embodiments, the second biocompatible polymeric layer is deposited onto the first biocompatible polymeric layer by first disposing an adhesive material on one or both of the biocompatible polymeric layers and then attaching the two layers via the adhesive material. In certain cases, the adhesive may be a heat sensitive adhesive or a pressure sensitive adhesive. In these embodiments, heat or pressure may be applied in order to bond the first and second biocompatible polymeric layers, thereby depositing the second biocompatible polymeric layer onto the first biocompatible polymeric layer.

In certain embodiments, the first biocompatible polymeric layer has an average thickness in the range of 1 µm to about 100 µm, e.g., 3 µm to 50 µm, including 5 µm to 20 µm, 5 µm to 15 µm, or 5 µm to 10 µm. For example, the first biocompatible polymeric may have an average thickness of about 1 µm, 3 µm, 5 µm, 8 µm, 10 µm, 12 µm, 15 µm, 20 µm, 30 µm, 40 µm, 50 µm, 60 µm, 70 µm, 80 µm, 90 µm, or 100 µm.

The first biocompatible polymeric layer may be poly(DL-lactide-co-glycolide) (PLGA), poly(DL-lactide-co-c-caprolactone) (DLPLCL), poly(c-caprolactone) (PCL), collagen, gelatin, agarose, poly(methyl methacrylate) (PMMA), galatin/c-caprolactone, collagen-GAG, collagen, fibrin, poly(lactic acid) (PLA), polyglycolic acid (PGA), PLA-PGA co-polymers, poly(anhydrides), poly(hydroxy acids), poly(ortho esters), poly(propylfumerates), poly(caprolactones), poly(hydroxyvalerate), polyamides, polyamino acids, polyacetals, biodegradable polycyanoacrylates, biodegradable polyurethanes and polysaccharides, polypyrrole, polyanilines, polythiophene, polystyrene, polyesters, non-biodegradable polyurethanes, polyureas, poly(ethylene vinyl acetate), polypropylene, polymethacrylate, polyethylene, polycarbonates, poly(ethylene oxide), co-polymers of the above, mixtures of the above, and adducts of the above, or combinations thereof.

In certain embodiments, the second biocompatible polymeric layer has an average thickness in the range of 1 µm to about 100 µm, e.g., 3 µm to 50 µm, including 5 µm to 30 µm, or 5 µm to 20 µm, or 5 µm to 15 µm. For example, the second biocompatible polymeric may have an average thickness of about 1 µm, 3 µm, 5 µm, 8 µm, 10 µm, 12 µm, 15 µm, 20 µm, 30 µm, 40 µm, 50 µm, 60 µm, 70 µm, 80 µm, 90 µm, or 100 µm.

The second biocompatible polymeric layer may be PLGA, DLPLCL, PCL, collogen, gelatin, agarose, poly(methyl methacrylate), galatin/c-caprolactone, collagen-GAG, collagen, fibrin, PLA, PGA, PLA-PGA co-polymers, poly(anhydrides), poly(hydroxy acids), poly(ortho esters), poly(propylfumerates), poly(caprolactones), poly(hydroxyvalerate), polyamides, polyamino acids, polyacetals, biodegradable polycyanoacrylates, biodegradable polyurethanes and polysaccharides, polypyrrole, polyanilines, polythiophene, polystyrene, polyesters, non-biodegradable polyurethanes, polyureas, poly(ethylene vinyl acetate), polypropylene, polymethacrylate, polyethylene, polycarbonates, poly(ethylene oxide), co-polymers of the above, mixtures of the above, and adducts of the above, or combinations thereof.

In certain embodiments, the first biocompatible polymeric layer has a higher melting temperature than the second biocompatible polymeric layer. Thus the melting temperature of the first biocompatible polymeric layer may be higher than the melting temperature of the second biocompatible polymeric layer by 40° C. or more, e.g., 50° C. or more, including 60° C. or more, 70° C. or more, 80° C. or more, 90° C. or more, 100° C. or more, 110° C. or more, 120° C. or more, 130° C. or more, 140° C. or more, or 150° C. or more. In certain instances, the melting temperature of the first biocompatible polymeric layer is higher than the melting temperature of the second biocompatible polymeric layer by 200° C. or less, e.g., 180° C. or less, including 160° C. or less, 150° C. or less, 140° C. or less, 130° C. or less, 120° C. or less, 110° C. or less, or 100° C. or less. Thus, in certain instances the melting temperature of the first biocompatible polymeric layer is higher than the melting temperature of the second biocompatible polymeric layer by 40° C. to 200° C., e.g., by 60° C. to 180° C., including by 70° C. to 150° C., or by 80° C. to 130° C.

In certain embodiments, the first biocompatible polymeric layer has a higher glass transition temperature than the second biocompatible polymeric layer. Thus the glass transition temperature of the first biocompatible polymeric layer may be higher than the glass transition temperature of the second biocompatible polymeric layer by 100° C. or more, e.g., 120° C. or more, including 140° C. or more, 160° C. or more, 180° C. or more, 200° C. or more, or 220° C. or more. In certain instances, the glass transition temperature of the first biocompatible polymeric layer is higher than the glass transition temperature of the second biocompatible polymeric layer by 300° C. or less, e.g., 280° C. or less, including 260° C. or less, 240° C. or less, 220° C. or less, 200° C. or less, 180° C. or less, or 160° C. or less. Thus, in certain instances the glass transition temperature of the first biocompatible polymeric layer is higher than the glass transition temperature of the second biocompatible polymeric layer by 100° C. to 300° C., e.g., by 120° C. to 260° C., including by 140° C. to 240° C., or by 160° C. to 220° C.

In some embodiments, the first biocompatible polymeric layer includes PMMA and the second biocompatible polymeric layer includes PCL. Thus, in certain embodiments, the method of forming a plurality of nanowires on a biocompatible surface includes depositing a second biocompatible polymeric layer containing PCL onto a surface of a first biocompatible polymeric layer containing PMMA. In some embodiments, the method of forming a plurality of nanowires on a biocompatible surface includes depositing a layer of PCL onto a surface of a PMMA layer.

Contacting a Nanoporous Membrane with the Second Biocompatible Layer

After depositing a second biocompatible polymeric layer onto a first biocompatible polymeric layer, as described above, the second biocompatible polymeric layer is contacted with a nanoporous membrane (see, for example, FIGS. 1 and 9). Thus, after contacting the second biocompatible polymeric layer with a nanoporous membrane, a first surface of the second biocompatible polymeric layer is bonded to a surface of the first biocompatible polymeric layer, and a second surface of the second biocompatible polymeric layer opposite the first surface of the second biocompatible polymeric layer is juxtaposed with a porous surface of the nanoporous membrane.

The nanoporous membrane may be any suitable nanoporous membrane. In some cases the nanoporous membrane is an anodized metal oxide membrane. Methods of making an anodized metal oxide membrane is described, e.g., in U.S. Pat. No. 7,393,391, which are incorporated herein by reference. A suitable metal oxide may contain, e.g., aluminum, titanium or tin. In certain embodiments, the nanoporous membrane is an anodized aluminum oxide (AAO) nanoporous membrane. Suitable AAO membranes include Whatman® Anodisc membranes and Synkera Unikera™ membranes. In some embodiments, the nanoporous membrane is a nanoporous silica membrane. Methods of making an anodized metal oxide membrane is described, e.g., in Fine et al. (Adv Healthc Mater. 2013 2:632) and Fan et al. (J Am Chem Soc. 2003 125:5254), which are incorporated herein by reference.

The nanoporous membrane is characterized by having disposed therein an array of pores that penetrate the membrane from a first surface of the membrane to a second surface opposite to the first surface. In some cases the pores penetrating the membrane are substantially perpendicular to the plane of the membrane. In certain embodiments, the pores are arranged in a regular array, such as a regular hexagonal array, or a square array. The shape of the pores may be any convenient shape, including, but not limited to, circular, square, hexagonal, oval, rectangular, etc. The average diameter of the pores may range from 5 nm to 500 nm, e.g., 10 nm to 400 nm, including 10 nm to 300 nm, 10 to 200 nm, 50 nm to 200 nm, 80 nm to 160 nm, 100 nm to 300 nm, 140 nm to 260 nm, 200 nm to 360 nm, or 240 nm to 340 nm. In certain embodiments, the average diameter of the pores may be 10 nm, 18 nm, 20 nm, 35 nm, 55 nm, 80 nm, 100 nm, 120 nm, 150 nm, 190 nm, 200 nm, 250 nm, 290 nm, or 300 nm. The density of pores on the surface of the nanoporous membrane may be in the range of $10^6$ to $10^{10}$ pores/cm$^2$, e.g., $5 \times 10^6$ to $5 \times 10^8$ pores/cm$^2$, $10^7$ to $5 \times 10^8$ pores/cm$^2$, or $5 \times 10^7$ to $5 \times 10^8$ pores/cm$^2$. In some instances, the density of pores on the surface of the nanoporous membrane is about $10^6$ pores/cm$^2$, $10^7$ pores/cm$^2$, $10^8$ pores/cm$^2$, or $10^9$ pores/cm$^2$. The average thickness of the nanoporous membrane may be in the range of 15 to 150 μm, e.g., 20 to 120 μm, including 30 to 100 μm, or 30 to 80 μm. In some instances, the average thickness of the nanoporous membrane is about 15 μm, 20 μm, 30 μm, 50 μm, 80 μm, 100 μm, 120 μm, 150 μm, 200 μm, 250 μm, or 300 μm.

In certain embodiments, the method of forming a plurality of nanowires on a biocompatible surface includes the step of creating a micropattern in the nanoporous membrane. Thus, in some cases, the nanoporous membrane is patterned to specify regions on the biocompatible surface where the nanowires will be formed. The patterning may be achieved by any suitable method. In one embodiment, creating a micropattern on the nanoporous membrane includes photolithography. Thus, in some cases, the nanoporous membrane is patterned by covering over the pores on a first surface of the nanoporous membrane with a photoresist in a desired pattern such that nanowires are formed only where the pores remain accessible to the biocompatible surface when the patterned surface of the nanoporous membrane is contacted with the biocompatible surface. In some cases, the photoresist is a positive photoresist. Further aspects of patterning a biocompatible surface using photolithography is described below.

The nanoporous membrane may be patterned to allow nanowires to be formed in a region of any convenient pattern of shape. In some cases, the nanoporous membrane is patterned in to grooves of width ranging from 1 μm to 100 μm, such as 1 μm, 3 μm, 5 μm, 8 μm, 10 μm, 20 μm, 30 μm, 40 μm, 50 μm, 60 μm, 70 μm, 80 μm, 90 μm, or 100 μm, with equal spacing between the grooves, such that the nanopores are accessible to the biocompatible surface in the grooves but are not accessible between the grooves when the patterned surface of the nanoporous membrane is contacted with the biocompatible surface. In other instances, the nanoporous membrane may be patterned into different shapes, such as, but not limited to, a circle, square, rectangle, oval, triangle, hexagon, etc.

In certain embodiments, the method of forming a plurality of nanowires on a biocompatible surface includes the step of contacting the nanoporous membrane with the second biocompatible polymeric layer under heat. In certain embodiments, the nanoporous membrane, which may or may not be patterned, as described above, is brought into contact with a surface of the second biocompatible polymeric layer deposited over a first biocompatible polymeric layer, and the second biocompatible polymeric layer is heated to a temperature sufficient to melt the second biocompatible polymeric layer. Thus, in some instances, the temperature is higher than the melting temperature of the polymeric material comprising the second biocompatible polymeric layer, e.g., 80° C. In certain embodiments, the temperature is raised for a sufficient amount of time such that the melted second biocompatible polymeric layer extrudes into the accessible pores (i.e., pores that are not covered with photoresist) of the nanoporous membrane that is in contact with the second biocompatible polymeric layer. Thus, in certain embodiments, the nanoporous membrane is contacted with a surface of the second biocompatible polymeric layer deposited over a first biocompatible polymeric layer, under conditions sufficient to extrude at least part of the second biocompatible polymeric layer into the accessible pores of the nanoporous membrane that is in contact with the second biocompatible polymeric layer. In certain embodiments, the nanoporous membrane is brought into contact with a surface of the second biocompatible polymeric layer deposited over a first biocompatible polymeric layer, and the second biocompatible polymeric layer is heated above the melting temperature of the polymeric material comprising the second biocompatible polymeric layer for a sufficient amount of time to cause the second biocompatible polymeric layer to extrude into the accessible pores of the nanoporous membrane that is in contact with the second biocompatible polymeric layer. In some instances, the second biocompatible polymeric layer is heated to about 80° C. for about 5 minutes after the nanoporous membrane is contacted with a surface of the second biocompatible polymeric layer deposited over a first biocompatible polymeric layer.

Forming a Plurality of Nanowires

Further aspects of the present disclosure include a method of forming a plurality of nanowires on a biocompatible surface including the step of forming a plurality of nanowires on the second biocompatible polymeric layer using the nanoporous membrane as a template (see, for example, FIGS. 1 and 9). Thus, in some embodiments, after contacting the nanoporous membrane with a surface of the second biocompatible polymeric layer deposited over a first biocompatible polymeric layer, the nanoporous membrane is used as a template, i.e., a mold, to form a plurality of nanowires from the second biocompatible polymeric layer. Thus, in some instances, at least a part of the second biocompatible polymeric layer is extruded into the accessible pores of the nanoporous membrane that is in contact with the second biocompatible polymeric layer.

Extruding the second biocompatible polymeric layer into the pores of the nanoporous membrane may be achieved by any suitable method. As described above, in certain embodiments, the second biocompatible polymeric layer is heated to a temperature above the melting temperature of the polymeric material comprising the second biocompatible polymeric layer, thereby melting and extruding at least a portion of the second biocompatible polymeric layer into the accessible pores of the nanoporous membrane. In some instances, the second biocompatible polymeric layer may be dissolved using a solvent, e.g., a volatile solvent, thereby allowing the second biocompatible polymeric layer to extrude into the accessible pores of the nanoporous membrane that is in contact with the second biocompatible polymeric layer.

After the second biocompatible polymeric layer is extruded into the pores of the nanoporous membrane, as described above, the extruded portion of the second biocompatible polymeric layer is allowed to solidify, e.g., by lowering the temperature or through evaporation the solvent.

In certain embodiments, a method of forming a plurality of nanowires on a biocompatible surface includes the step of dissolving the nanoporous membrane after contacting the nanoporous membrane with the second biocompatible polymeric layer. Dissolving the nanoporous membrane exposes the nanowires that are formed from the extruded second biocompatible polymeric layer in the pores of the nanoporous membrane. Thus, in certain embodiments, the method of forming a plurality of nanowires on a biocompatible surface includes the step of dissolving the nanoporous membrane after contacting the nanoporous membrane with the second biocompatible polymeric layer under conditions sufficient to extrude at least part of the second biocompatible polymeric layer into the accessible pores of the nanoporous membrane that is in contact with a surface of the second biocompatible polymeric layer, thereby exposing the plurality of nanowires formed on the second biocompatible polymeric layer.

Dissolving the nanoporous membrane may be achieved in any convenient method. For example, dissolving the nanoporous membrane may include etching the nanoporous membrane with an alkaline solution, such as sodium hydroxide. Dissolving the nanoporous membrane may take any suitable amount of time. In some instances, the nanoporous membrane may be dissolved by etching the nanoporous membrane with a 0.5 M sodium hydroxide solution for about an hour.

In certain embodiments, when the nanoporous membrane is patterned with photoresist such that the nanowires are formed in a desired pattern on the second biocompatible polymeric layer, the dissolving step may also dissolve the photoresist on the nanoporous membrane. Thus in some embodiments, nanoporous membrane and the photoresist may be dissolved by etching the photoresist-patterned nanoporous membrane with an alkaline solution, such as sodium hydroxide.

An aspect of the present disclosure includes a method of forming a plurality of nanowires on a biocompatible surface by contacting a second biocompatible polymeric layer deposited over a first biocompatible polymeric layer with a nanoporous membrane under conditions sufficient to extrude at least part of the second biocompatible polymeric layer into the accessible pores of the nanoporous membrane, wherein the average length of the plurality of nanowires formed on the second biocompatible polymeric layer depends on the thickness of the second biocompatible polymeric layer. Thus, in some embodiments, the average length of a plurality of nanowires formed on a thinner second biocompatible polymeric layer is shorter than the length of a plurality of nanowires formed on a thicker second biocompatible polymeric layer. In certain embodiments, the average length of the plurality of nanowires formed on the second biocompatible polymeric layer can be controlled by solely controlling the thickness of the second biocompatible polymeric layer.

Creating a Micropattern in the First Biocompatible Polymeric Layer

Another aspect of the present disclosure includes a method of forming a plurality of nanowires on a biocompatible surface including creating a micropattern in the first biocompatible polymeric layer, thereby producing a microdevice that includes a plurality of nanowires on a biocompatible surface (FIGS. 1 and 9). In certain embodiments the first biocompatible polymeric layer is patterned into a micropattern, using, e.g., photolithography. Thus, in certain instances, the first biocompatible polymeric layer is provided on a substrate, e.g. a silicon wafer, and the first biocompatible polymeric layer is patterned by photolithography, i.e., by transferring a computer-designed photomask pattern to a photoresist-coated first biocompatible polymeric layer by etching. Creating the micropattern in the first biocompatible polymeric layer may be performed before depositing a second biocompatible polymeric layer onto the first biocompatible polymeric layer, as described above.

Either a positive or a negative photoresist may be used to define the dimensions and shape of the microdevice that includes a plurality of nanowires on a biocompatible surface. The photoresist may be deposited by dipping the substrate with the polymer layer in a solution containing the photoresist, by pipetting the photoresist solution onto the substrate, or by spin coating, for example. In certain cases, a positive photoresist may be used. A mask that defines the shape of the microdevice structures may be positioned over the photoresist. In certain embodiments, the mask may allow light to pass through a ring shaped region in the mask, thereby exposing a ring shaped region of the positive photoresist to light and making the photoresist in the ring shaped region soluble to the photoresist developer. Accordingly, upon development of the photoresist, ring shaped region of the photoresist is removed.

In other embodiments, the photoresist may be a negative photoresist. In these embodiments, the mask may be designed to allow light to pass through a circular region in the mask, thereby exposing a circular region of the negative photoresist to light and making the photoresist in the ring shaped region surrounding the circular region soluble to the photoresist developer. Accordingly, upon development of the photoresist, a ring shaped region of the photoresist is removed.

A variety of positive and negative photoresists may be used in the methods disclosed herein. As used herein, the phrase "positive photoresist" refers to a type of photoresist in which the portion of the photoresist that is exposed to light becomes soluble to the photoresist developer. While, the portion of the photoresist that is unexposed remains insoluble to the photoresist developer. As used herein, the phrase "negative photoresist" refers to a type of photoresist in which the portion of the photoresist that is exposed to light becomes insoluble to the photoresist developer. While, the unexposed portion of the photoresist is dissolved by the photoresist developer. For example, the photoresist may be Hoechst Ariz. 4620, Hoechst Ariz. 4562, AZ 1500, e.g., AZ 1514 H, Shipley 1400-17, Shipley 1400-27, Shipley 1400-37, etc.

Other shapes of the microdevice structures, such as square, triangular, oval, diamond, etc., may also be defined by using an appropriately designed mask. The surface area of the microdevice may be determined by the surface area of the area in the photomask through which the light passes. In certain cases, the microdevice may be circular in shape and have an average diameter in the range of about 10 µm-1000 µm, for example, 10 µm-500 µm, 10 µm-300 µm, 10 µm-250

µm, 10 µm-200 µm, e.g., 10 µm, 20 µm, 40 µm, 50 µm, 60 µm, 70 µm, 80 µm, 90 µm, 100 µm, 130 µm, 150 µm, 180 µm, 200 µm, 250 µm, 300 µm, 400 µm, or 500 µm. In certain cases, the microdevice may be square in shape and have an average width and length in the range of about 10 µm-1000 µm, for example, 10 µm-500 µm, 10 µm-300 µm, 10 µm-250 µm, 10 µm-200 µm, e.g., 10 µm, 20 µm, 40 µm, 50 µm, 60 µm, 70 µm, 80 µm, 90 µm, 100 µm, 130 µm, 150 µm, 180 µm, 200 µm, 250 µm, 300 µm, 400 µm, or 500 µm.

The photomask may be generated by standard procedure based on the desired pattern of the microdevices to be manufactured. As described above, the image for the photomask defines the shape and dimension of the microdevices.

Light may be used to expose a defined region of the photoresist layer via the mask. In certain cases, light may be a short wavelength light (for example, a wavelength of about 100 nm-440 nm), such as, ultra violet (UV) light, deep UV light, H and I lines of a mercury-vapor lamp. The step of exposing the photoresist to light may be followed with a step of photoresist development where the photoresist is contacted with a photoresist developer. In embodiments, where a positive photoresist is used, the regions of the positive photoresist layer exposed to light are washed away in the photoresist developer. In embodiments, where a negative photoresist is used, the regions of the negative photoresist layer not exposed to light are washed away in the photoresist developer.

Any standard photoresist developer compatible with the photoresist deposited may be used in the methods described herein. As such, a positive developer may be used to remove any positive photoresist exposed to light. In certain cases, a negative developer may be used to remove any negative photoresist not exposed to light.

The regions of the polymer layer from which the photoresist has been removed are then etched to remove the biocompatible polymer layer. The portion or portions of the biocompatible polymer layer that are covered by the photoresist form the microdevice. A dry or wet etching process as is standard in the art may be used to remove the exposed biocompatible polymer layer. In certain cases, the etching process is reactive ion etching. Standard procedures and apparatus for etching may be used. For example, reactive ion etching methods and apparatus are described in U.S. Pat. Nos. 6,669,807, 5,567,271, which are herein incorporated by reference. The etching is carried out for a length of time sufficient to remove all of the polymer material not covered with the photoresist such that the plurality of microdevice structures are not connected together via any residual polymer material.

Following the etching step, the photoresist may be removed using any standard photoresist remover or photoresist stripper compatible with the photoresist used. Exemplary photoresist removers include 1-methyl-2-pyrrolidon, dimethyl sulfoxide, AZ® 100 Remover, and the like.

The plurality of microdevice structures generated by the foregoing method may be 2, 5, 10, 20, 50, 100, 500, 1000, 1500, 2000, 2500, 3000, 3500, 4000, 4500, 5000, 5500, 6000, 6500, or more, for example, 1000-100,000 microdevices may be generated, such as 2000-80,000, or about 3000-70,000. In certain embodiments, the microdevices are patterned as an array on a substrate.

"Etching" as used herein refers to removing the polymer completely or substantially completely, for example, in embodiments where the planar layer of biocompatible material is, for example, 10 µm thick, "etching" or "complete etching" removes the polymer to a depth of about 10 µm, such as, a depth of 9.999 µm, 9.5 µm, 9.2 µm. In general, "etching" or "complete etching" removes the polymer to an extent such that the individual microdevices fabricated on a substrate are no longer connected to each other as a result of the polymer present in between the microdevices not being completely removed. As such, "etching" or "complete etching" provides for microdevices that when removed from the substrate are released as individual microdevices instead of being connected by residual polymer layer.

In some embodiments, wherein the first biocompatible polymeric layer is provided on a first substrate, e.g., a first silicon wafer, and micropatterned by photolithography, depositing the second biocompatible polymeric layer onto the first biocompatible polymeric layer may be achieved by heating the first biocompatible polymeric layer and contacting a surface of the heated first biocompatible polymeric layer with a second biocompatible polymeric layer spun-cast onto a second substrate, e.g., a second silicon wafer (FIGS. 1 and 9). In such cases, the second biocompatible polymeric layer may become bonded to the first biocompatible polymeric layer according to the micropattern created on the first biocompatible polymeric layer. Subsequently, separating the wafers causes the second biocompatible polymeric layer to lift off onto the micropatterned first biocompatible polymeric layer, thereby depositing the second biocompatible polymeric layer over the micropatterned first biocompatible polymeric layer, wherein both layers have the same micropattern.

Figure 2:
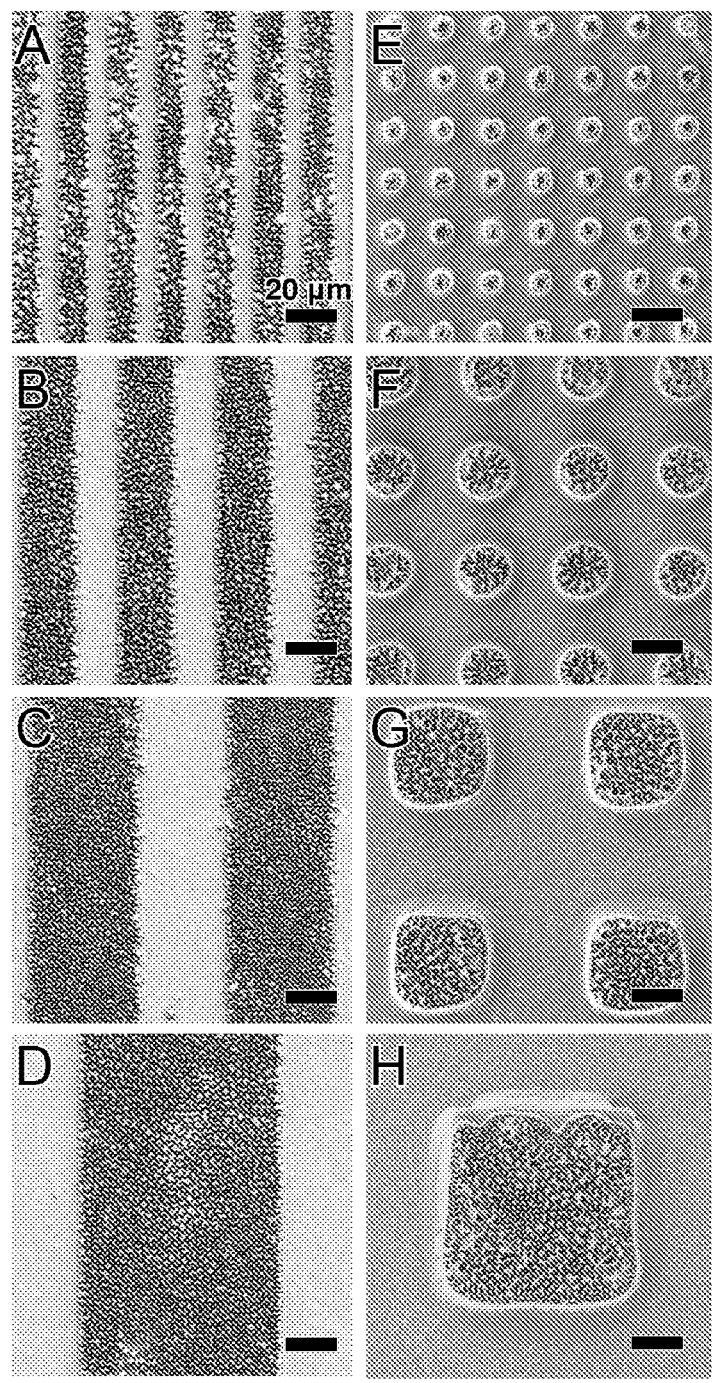
FIG. 2 shows scanning electron microscope (SEM) micrographs of nanowire-coated microdevices, according to embodiments of the present disclosure.
Figure 5:
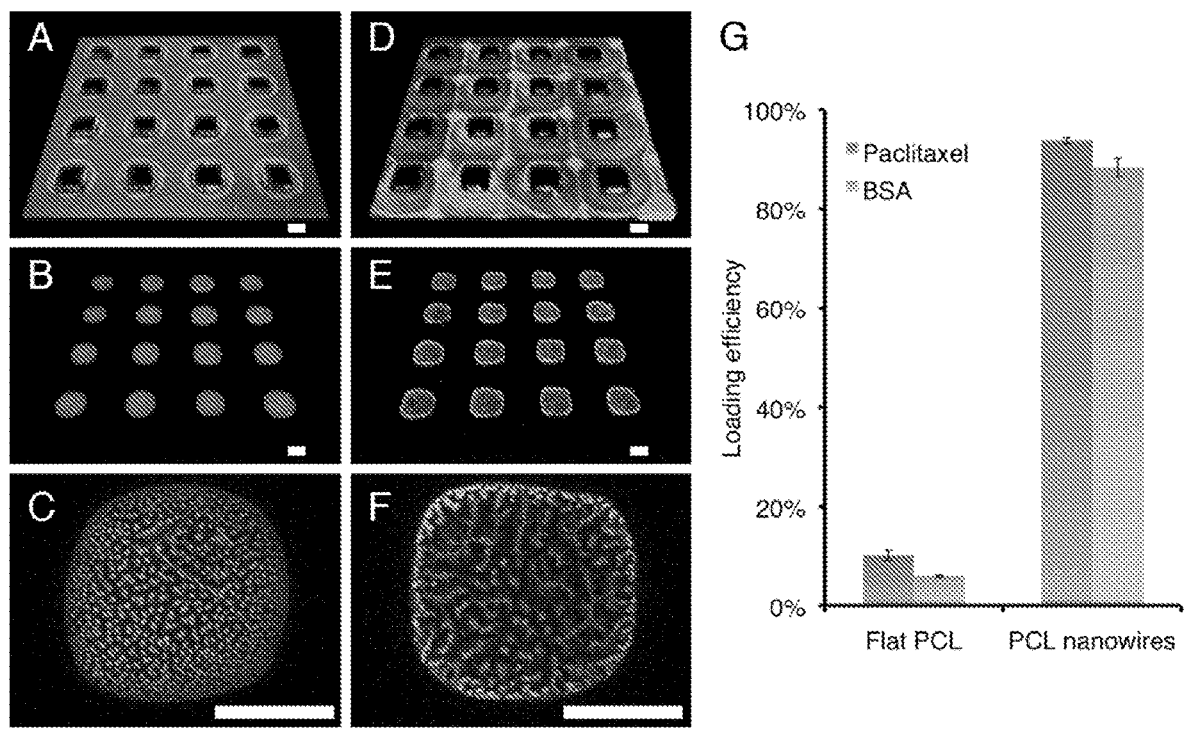
FIG. 5 shows three-dimensional confocal imaging reconstructions of arrays of fluorescently detectable active agent-loaded microdevices, according to embodiments of the present disclosure, as well as control microdevices, and measurements of loading efficiency.
Figure 6:
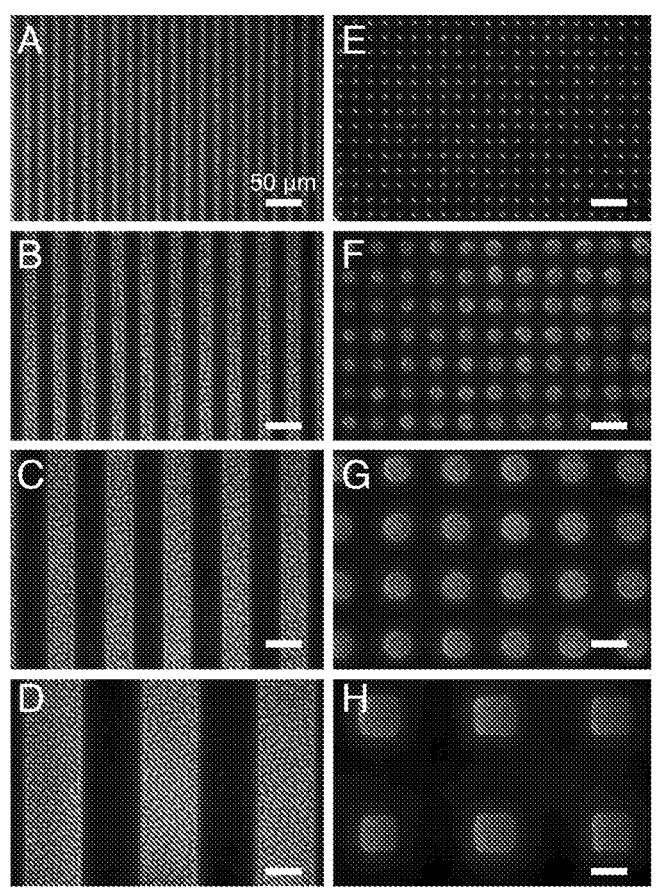
FIG. 6 shows fluorescent images of arrays of fluorescently detectable active agent-loaded microdevices, according to embodiments of the present disclosure.

In certain embodiments, creating a micropattern on a first biocompatible polymeric layer and subsequently forming a plurality of nanowires from the second biocompatible surface deposited over the first biocompatible polymeric layer, as described above, defines the dimensions of a microdevice that includes a first biocompatible polymeric layer and a plurality of nanowires formed from a second biocompatible polymeric layer disposed on the first biocompatible polymeric layer. In certain embodiments, the first biocompatible polymeric layer is provided on a substrate, e.g., a silicon wafer, and creating a micropattern on the first biocompatible polymeric layer produces an array of micropatterned first biocompatible polymeric layers on the substrate (FIGS. 2, 5 and 6). In such cases, certain embodiments of the subject method produces a plurality of microdevices, each comprising a first biocompatible polymeric layer disposed on the substrate and a plurality of nanowires formed from a second biocompatible polymeric layer disposed on the first biocompatible polymeric layer, according to the pattern of the array. The individual microdevices may be detached from the substrate by scraping the substrate and the microdevices may be used in various applications, as described further below.

Microdevices

Also provided herein are microdevices containing a plurality of nanowires disposed on a biocompatible surface, wherein the microdevices are formed by a process including a method of forming a plurality of nanowires on a biocompatible surface, as described above. In certain embodiments, the microdevice includes a plurality of nanowires disposed on a biocompatible surface, wherein the biocompatible surface includes a first biocompatible polymeric layer and a plurality of nanowires formed from a second biocompatible polymeric layer disposed on a surface of the first biocompatible polymeric layer. In certain embodiments, the subject microdevices are characterized in that the plurality of nanowires are derived from the second biocompatible polymeric layer, e.g., by extruding at least part of the second biocompatible polymeric layer into the pores of a nanoporous membrane, thereby molding the polymeric material of the second biocompatible polymeric layer using the pores of the nanoporous membrane as a template, as described above. Thus, in certain embodiments, the nanowires are biocompatible nanowires formed from the same polymeric material, e.g., PCL, as the second biocompatible polymeric layer.

In certain embodiments, the subject microdevices are characterized in that the plurality of nanowires are disposed on a biocompatible surface in such a way that the nanowires substantially protrudes out of the biocompatible surface of the microdevice. Thus, in certain embodiments, a first end of a nanowire is attached to the biocompatible surface and a second end is unattached and is oriented distally to the surface of the microdevice (FIGS. 1, 3, 9 and 10). The attached end of a nanowire may be said to be the proximal end and the unattached end of a nanowire may be defined as the distal end of the nanowire. Thus, in certain embodiments, a nanowire of the plurality of nanowires disposed on a biocompatible surface of a microdevice, wherein the biocompatible surface includes a first biocompatible polymeric layer and the plurality of nanowires formed from a second biocompatible polymeric layer disposed on a surface of the first biocompatible polymeric layer, has an attached proximal end and an unattached or free distal end. In certain embodiments, a nanowire is attached at the proximal end directly to the second biocompatible polymeric layer. In certain embodiments, a nanowire is attached at the proximal end directly to the first biocompatible polymeric layer. In certain embodiments, each nanowire of the plurality of nanowires is attached at the proximal end directly to the first or second biocompatible polymeric layers.

In certain embodiments, the subject microdevices are characterized in that the plurality of nanowires are disposed on a biocompatible surface such that the nanowires are present only on one surface of the microdevice. Thus, in certain embodiments, the microdevice includes a substantially flat, planar surface formed by a first surface of the first biocompatible polymeric layer, and includes a plurality of nanowires formed from a second biocompatible polymeric layer disposed on a second surface opposite the first surface of the first biocompatible polymeric layer, wherein the plurality of nanowires is disposed on a surface opposite to the substantially flat, planar surface of the microdevice.

In certain embodiments, the nanowires have an average diameter in the range of 20 nm to 500 nm, e.g., 50 nm to 400 nm, including 100 nm to 350 nm, 140 to 320 nm. In some embodiments, the nanowires have a diameter that range from 20 to 600 nm, e.g., from 40 nm to 500 nm, including 60 nm to 450 nm, 80 nm to 420 nm, 20 nm to 300 nm, 50 nm to 250 nm, 80 nm to 220 nm, 50 nm to 350 nm, 80 nm to 300 nm, 100 nm to 280 nm, 100 nm to 500 nm, 150 nm to 450 nm, or 180 nm to 420 nm. Thus, the average diameter of the nanowires may be 50 nm, 80 nm, 100 nm, 110 nm, 120 nm, 130 nm, 140 nm, 150 nm, 160 nm, 170 nm, 180 nm, 200 nm, 250 nm, 290 nm, 300 nm, 320 nm, 330 nm or 350 nm. The density of nanowires on the surface of the second biocompatible polymeric layer may be in the range of $10^6$ to $10^{10}$ nanowires/cm$^2$, e.g., $5 \times 10^6$ to $5 \times 10^8$ nanowires/cm$^2$, $10^7$ to $5 \times 10^8$ nanowires/cm$^2$, or $5 \times 10^7$ to $5 \times 10^8$ nanowires/cm$^2$. In some instances, the density of nanowires on the surface of the second biocompatible polymeric layer is about $10^6$ nanowires/cm$^2$, $10^7$ nanowires/cm$^2$, $10^8$ nanowires/cm$^2$, or $10^9$ nanowires/cm$^2$. The average length of the nanowires may be in the range of 2 to 14 µm, e.g., 2 to 4 µm, 5 to 9 µm, or 10 to 14 µm. In certain instances, the length of the nanowires may range from 2 to 15 µm, e.g., 2 to 5 µm, 5 to 10 µm, or 10 to 15 µm. The diameter, distribution density and length of the nanowires may be determined by analyzing scanning electron microscopy (SEM) micrographs.

In certain embodiments, the subject microdevices containing a plurality of nanowires disposed on a biocompatible surface allow for enhanced adhesion to an epithelial surface, such as a mucosal surface. Adhesion to an epithelial surface may be measured by placing a nanowire-coated surface of a microdevice onto a layer of Caco-2 cells for 10 minutes, followed by exposure to increasing shear forces at 5 minute intervals, and determining the fraction of microdevices remaining after exposure to each shear force. In certain embodiments, the fraction of microdevices containing a plurality of nanowires disposed on a biocompatible surface and placed on an epithelial surface remaining after exposure to a shear force of up to 1 dyne/cm$^2$ is 0.4 or greater, e.g., 0.45 or greater, 0.475 or greater, 0.5 or greater, 0.525 or greater, or 0.55 or greater, such as 0.9 or less, e.g., 0.85 or less, 0.8 or less, 0.75 or less, 0.7 or less, 0.65 or less, or 0.6 or less, such as between 0.4 and 0.9, e.g., 0.45 and 0.85, 0.5 and 0.8, or 0.55 and 0.7. In certain embodiments, the fraction of microdevices containing a plurality of nanowires disposed on a biocompatible surface and placed on an epithelial surface remaining after exposure to a shear force of up to 10 dyne/cm$^2$ is 0.3 or greater, e.g., 0.325 or greater, 0.35 or greater, or 0.375 or greater, such as 0.9 or less, e.g., 0.80 or less, 0.7 or less, 0.6 or less, 0.55 or less, 0.5 or less, or 0.4 or less, such as between 0.3 and 0.9, e.g., 0.34 and 0.8, 0.36 and 0.7, or 0.38 and 0.6. In certain embodiments, the fraction of microdevices containing a plurality of nanowires disposed on a biocompatible surface and placed on an epithelial surface remaining after exposure to a shear force is larger than the fraction of microdevices without nanowires and placed on an epithelial surface remaining after exposure to the shear force, by 0.15 or more, e.g., 0.2 or more, 0.25 or more, 0.3 or more, 0.35 or more, or 0.4 or more, such as 0.6 or less, 0.55 or less, 0.5 or less, or 0.45 or less, and may be in the range of 0.15 to 0.6, e.g., 0.2 to 0.55, including 0.25 to 0.5, or 0.3 to 0.45.

In certain embodiments, a microdevice containing a plurality of nanowires disposed on a biocompatible surface is disposed on a solid substrate, e.g., a silicon wafer. In certain embodiments, a plurality of microdevices containing a plurality of nanowires disposed on a biocompatible surface is disposed on a solid substrate, e.g., a silicon wafer. In such instances, the microdevices may be micropatterned on the substrate using photolithography, to form an array of microdevices, as described above. In some instances, the microdevices containing a plurality of nanowires disposed on a biocompatible surface formed in an array on the substrate are detachable microdevices. For example, these microdevices formed in an array on the substrate may be detached from the substrate with a scraping device, e.g., a razor blade, a scalpel, a spatula, a scraper, and the like.

Active Agents and Method of Loading a Microdevice Therewith

In certain embodiments, the microdevice includes an active agent disposed on the plurality of nanowires. The active agent may be disposed on the plurality of nanowires using any convenient method. In certain embodiments, the active agent is loaded onto a microdevice containing a plurality of nanowires disposed on a biocompatible surface by contacting the microdevice with a solution that contains an active agent. For example, the agent may be disposed onto the plurality of nanowires by releasing a solution containing the agent on the surface of the nanowires, using a pipette, such as a micropipette, or a nanopipette. In certain cases, the agent may be loaded onto the nanowires of the microdevices using an automatic or semi-automatic dispensing device.

In certain embodiments, contacting the microdevice with a solution that contains an active agent is followed by drying the microdevice. Any suitable method may be used to dry the microdevice. Drying may include air-drying, heating, applying a stream of gas, such as an inert gas, or a combination thereof. In certain embodiments, the drying includes air-drying. In certain embodiments, the microdevice is air-dried by inverting the microdevice such that the surface of the microdevice containing the nanowires faces down.

In certain embodiments, the active agent may be disposed on the plurality of nanowires by releasing a small volume of a solution of the agent onto the surface of the nanowires. In certain embodiments, the nanowires may be elevate, for example, the nanowires may be present on a plane higher than the plane on which the first biocompatible material is disposed. In certain cases, the first biocompatible material may be disposed on a substrate and the nanowires may be present on the surface of the first biocompatible material and thus elevated with respect to the surface of the substrate. These elevated nanowires may be contacted with a dispenser for dispensing a solution of an agent of interest. In certain embodiments, deposition of an agent onto the elevated nanowires may results in containment of the solution onto the surface of the nanowires such that the solution does not flow onto the surface of the substrate. Thus, the microdevice may be loaded with an agent with minimal wasting, such as, due to loss of the agent from flowing on to surface of the substrate. In certain cases, the agent may be loaded on the nanowires while the nanowires are present on the substrate and the microdevices with loaded nanowires may then be separated from the substrate.

The concentration of the active agent that is loaded onto a microdevice containing a plurality of nanowires disposed on a biocompatible surface may vary depending on the active agent and the intended therapeutic use for the microdevice, e.g., the intended target tissue to which the microdevice is to be delivered. In certain embodiments, the active agent may be loaded at a concentration ranging from 0.01 µg/cm$^2$ to 1 mg/cm$^2$, e.g., 0.1 µg/cm$^2$ to 100 µg/cm$^2$, 0.5 µg/cm$^2$ to 50 µg/cm$^2$, or 1 µg/cm$^2$ to 10 µg/cm$^2$, wherein the area is the total area of the microdevice surface that contains the plurality of nanowires.

In some embodiments, the subject microdevice containing a plurality of nanowires disposed on a biocompatible surface allows for efficient loading of an active agent. "Loading efficiency," as used herein, refers to the relative proportion of the total amount of active agent present on the microdevice surface that is localized to the surface containing the plurality of nanowires. The loading efficiency may be measured by, e.g., loading the microdevice with a fluorescently detectable active agent, such as Oregon Green 488 paclitaxel or fluorescein isothiocyanate (FITC)-bovine serum albumin (BSA), as described above, and then imaging the loaded microdevices with a confocal microscope to determine the localization of the fluorescently detectable active agent. In certain embodiments, a plurality of microdevices may be patterned into an array on a substrate, such as a silicon wafer, and the nanowires disposed on a surface of each of the plurality of microdevices may allow for efficient loading of an active agent on the microdevices when the substrate is contacted with a solution containing the active agent. In such embodiments, the loading efficiency of a patterned array of a plurality of microdevices containing a plurality of nanowires disposed on a biocompatible surface is 60% or greater, e.g., 65% or greater, 70% or greater, 75% or greater, 80% or greater, 82% or greater, 84% or greater, 86% or greater, 88% or greater, or 90% or greater, such as 98% or less, e.g., 95% or less, 93% or less, 91% or less, or 90% or less, and in some cases ranges from 60% to 98%, e.g., from 65% to 95%, including from 70% to 94%, from 75% to 93%, or from 80% to 90%. In some embodiments, the loading efficiency of a patterned array of a plurality of microdevices containing a plurality of nanowires disposed on a biocompatible surface by percentage is higher than the loading efficiency of a patterned array of a plurality of microdevices that do not contain nanowires by 50% or more, e.g., 55% or more, 60% or more, 65% or more, 70% or more, 75% or more, or 80% or more, such as 90% or more, e.g., 88% or less, 85% or less, 83% or less or 81% or less, and in some cases by a range from 55% to 90%, e.g., 60% to 88%, 65% to 85%, 70% to 83%, or 75% to 81%.

In some instances, the subject microdevice containing a plurality of nanowires disposed on a biocompatible surface has enhanced permeation of active agents loaded onto the nanowires across an epithelial surface to which the biocompatible nanowire-coated surface is attached. Permeation of active agent may be measured by, e.g., loading a microdevice with BSA may be placed on a monolayer of Caco-2 cells in the apical chamber of a transwell insert, and the amount of BSA permeating through the Caco-2 cell monolayer to the basolateral chamber can be measured over a time period, such as over 18 hours. In certain embodiments, microdevices containing a plurality of nanowires disposed on a biocompatible surface has a higher rate of permeation across an epithelial surface to which the biocompatible nanowire-coated surface is attached than a micro device that does not contain nanowires by 1.2 fold or more, e.g., 1.4 fold or more, 1.6 fold of more, 1.8 fold or more, 2.0 fold or more, 2.2 fold or more, or 2.4 fold or more, such as, 3.0 fold or less, 2.8 fold or less, 2.6 fold or less, or 2.5 fold or less, and may be higher by a range of 1.2 to 3.0 fold, e.g., 1.3 to 2.8 fold, 1.4 to 2.6 fold, or 1.5 to 2.5 fold.

In certain instances, the active agent is a bioactive agent. In some embodiments, the bioactive agent is selected from a polypeptide, growth factor, a steroid, an antibody, an antibody fragment, a DNA, an RNA, and siRNA, an antimicrobial agent, an antibiotic, an antiretro viral drug, an anti-inflammatory compound, an antitumor agent, anti-angiogeneic agent, and a chemotherapeutic agent. The bioactive agents may be in a purified form, partially purified form, recombinant form, or any other form appropriate for inclusion in the microdevices. In general, the bioactive agents are free of impurities and contaminants.

Exemplary bioactive agents that may be incorporated in the microdevices are sugars, carbohydrates, peptides, nucleic acids, aptamers, small molecules, large molecules, vitamins; inorganic molecules, organic molecules, proteins, co-factors for protein synthesis, antibody therapies, such as Herceptin®, Rituxan®, Myllotarg®, and Erbitux®; hormones, enzymes such as collagenase, peptidases, and oxidases; antitumor agents and chemotherapeutics such as cis-platinum, ifosfamide, methotrexate, and doxorubicin hydrochloride; immuno-suppressants; permeation enhancers such as fatty acid esters including laureate, myristate, and stearate monoesters of polyethylene glycol; bisphosphonates such as alendronate, clodronate, etidronate, ibandronate, (3-amino-1-hydroxypropylidene)-1,1-bisphosphonate (APD), dichloromethylene bisphosphonate, aminobisphosphonatezolendronate, and pamidronate; pain killers and anti-inflammatories such as non-steroidal anti-inflammatory drugs (NSAID) like ketorolac tromethamine, lidocaine hydrochloride, bipivacaine hydrochloride, and ibuprofen; antibiotics and antiretroviral drugs such as tetracycline, vancomycin, cephalosporin, erythromycin, bacitracin, neomycin, penicillin, polymycin B, biomycin, chloromycetin, streptomycin, cefazolin, ampicillin, azactam, tobramycin, clindamycin, gentamicin, and aminoglycocides such as tobramycin and gentamicin; and salts such as strontium salt, fluoride salt, magnesium salt, and sodium salt.

Examples of antimicrobial agents include, but are not limited to, tobramycin, amoxicillin, amoxicillin/clavulanate, amphotericin B, ampicillin, ampicillin/sulbactam, atovaquone, azithromycin, cefazolin, cefepime, cefotaxime, cefotetan, cefpodoxime, ceftazidime, ceftizoxime, ceftriaxone, cefuroxime, cefuroxime axetil, cephalexin, chloramphenicol, clotrimazole, ciprofloxacin, clarithromycin, clindamycin, dapsone, dicloxacillin, doxycycline, erythromycin, fluconazole, foscarnet, ganciclovir, atifloxacin, imipenem/cilastatin, isoniazid, itraconazole, ketoconazole, metronidazole, nafcillin, nafcillin, nystatin, penicillin, penicillin G, pentamidine, piperacillin/tazobactam, rifampin, quinupristin-dalfopristin, ticarcillin/clavulanate, trimethoprim/sulfamethoxazole, valacyclovir, vancomycin, mafenide, silver sulfadiazine, mupirocin, nystatin, triamcinolone/nystatin, clotrimazole/betamethasone, clotrimazole, ketoconazole, butoconazole, miconazole, and tioconazole.

Antiangiogenic agents include, but are not limited to, interferon-α, COX-2 inhibitors, integrin antagonists, angiostatin, endostatin, thrombospondin-1, vitaxin, celecoxib, rofecoxib, JTE-522, EMD-121974, and D-2163, FGFR kinase inhibitors, EGFR kinase inhibitors, VEGFR kinase inhibitors, matrix metalloproteinase inhibitors, marmiastat, prinomastat, BMS275291, BAY12-9566, neovastat, rhuMAb VEGF, SU5416, SU6668, ZD6474, CP-547, CP-632, ZD4190, thalidomide and thalidomide analoges, sqalamine, celecoxib, ZD6126, TNP-470, and other angiogenesis inhibitor drugs.

In some embodiments, the bioactive agent is a small molecule, such as but not limited to an anti-inflammatory drug, an immunosuppressant drug, a vitamin, micronutrient or antioxidant, an antibacterial drug (e.g., vancomycin or cephazolin), an anti-viral drug (e.g., gancyclovir, acyclovir or foscarnet), an anti-fungal drug (e.g., amphotericin B, fluconazole or voriconazole) or an anti-cancer drug (e.g., cyclophosphamide or melphalan). In certain embodiments, the small molecule is a vitamin, micronutrient or antioxidant, such as but not limited to, vitamin A, vitamin C, vitamin E, zinc, copper, lutein or zeaxanthin. In certain embodiments, the small molecule is an immunosuppressant drug, such as but not limited to, cyclosporine, methotrexate or azathioprine. In certain embodiments, the small molecule is an anti-inflammatory drug, such as but not limited to, a corticosteroid (e.g., triamcinolone acetonide or dexamethasone) or a non-steroidal drug (e.g., ketorolac or diclofenac).

In certain embodiments, the large molecule drug is an immunosuppressant drug, such as but not limited to, etanercept, infliximab or daclizumab. In certain embodiments, the large molecule drug is a neuromuscular blocker drug, such as but not limited to, botulinum toxin A. In certain embodiments, the large molecule drug is a complement inhibitor, such as but not limited to, an anti-C3 compound.

In certain embodiments, the bioactive agent may be Mesalazine, also known as Mesalamine, or 5-aminosalicylic acid (5-ASA), prednisone, TNF inhibitor, azathioprine (Imuran), methotrexate, or 6-mercaptopurine, aminosalicylate anti-inflammatory drugs, corticosteroids, azathioprine, mercaptopurine, methotrexate, infliximab, adalimumab, certolizumab, natalizumab, and hydrocortisone, statins, e.g., atorvastatin, such as atorvastatin calcium, anti-psychotic drugs, e.g., olanzapine.

In certain cases, the bioactive agent may be combined with a pharmaceutically acceptable additive before or after placement of the bioactive agent on a layer of the subject device. The term "pharmaceutically acceptable additive" refers to preservatives, antioxidants, emulsifiers, dyes and excipients known or used in the field of drug formulation and that do not unduly interfere with the effectiveness of the biological activity of the active agent, and that is sufficiently non-toxic to the patient. For example, the bioactive agent may be formulated with inert fillers, anti-irritants, gelling agents, stabilizers, surfactant, emollients, coloring agents, preservatives, or buffering agents, as are known in the art. The term "excipients" is conventionally known to mean carriers, diluents and/or vehicles used in formulating drug compositions effective for the desired use.

Utility

The subject microdevices formed according to the methods of the present disclosure find use in many applications. The nanoscale and microscale features of the subject microdevices promote cellular adhesion and enhance attachment of the microdevice to epithelial surfaces, such as a mucosal surface. The micropatterned nanowire-coated microdevice arrays of the subject disclosure also provide high-throughput, low-waste, loading of active agents. Thus the nanowires serve as a drug reservoir. The nanowires of the subject microdevice facilitate adhesion of the microdevice to monolayers of epithelial cells and unidirectional drug release toward the epithelial tissue.

In general, the subject method produces microdevices that are substantially planar, and provide for release of the bioactive agent(s) deposited in the nanowires of the microdevice from the biocompatible surface of the microdevice. As such, the release of the bioactive agents is substantially in a single direction in contrast to bioactive agents release from a capsule, tablet, or microsphere. The nanowires mediate attachment of the microdevice to the surface of a target tissue, such as, to epithelial cells of a mucosal lining of the gastrointestinal tract. The combination of attachment of the nanowires of the microdevice to the target tissue and release of the bioactive agent from the nanowires provides a localized release of the bioactive agent in close proximity to the target tissue, thereby providing a higher effective concentration of bioactive agent available for uptake by the cells and/or permeation through the epithelial layer. As such, the microdevice lowers the amount of bioactive agent that may be required to treat a condition. In addition, the attachment of the microdevice to the target tissue may increase the residence time of the microdevice near the target tissue. For example, attachment of the microdevice to the epithelial lining of the gastrointestinal tract increases its residence time in the gastrointestinal tract as the attached microdevice may be better able to resistant peristaltic motion of the gastrointestinal tract. Moreover, the microdevice may be sized to increase the surface area available to attach to the cells of the target tissue while simultaneously being resistant to the shear stress that may be present in the target tissue.

In certain embodiments, the subject microdevices formed according to the methods of the present disclosure find use in delivering an active agent to a mucosal surface in a subject, e.g., a patient in need of treatment. In some embodiments, the microdevices may be loaded with an active agent, as described above, and the active agent is delivered to a mucosal surface of a patient in need of treatment by contacting the plurality of nanowires of the microdevice disposed with the active agent to the mucosal surface. The microdevice may be delivered to the subject by any suitable method, including oral, nasal, anal, vaginal, transcutaneous, surgical routes, etc. The microdevice may be delivered in a capsule, tablet or microsphere. In some embodiments, the microdevice may be suspended in a physiologically compatible solution, e.g. saline solution. Delivery may be through a syringe, catheter, directly placing, etc. Methods of delivering a microdevice are described in, e.g., U.S. Appl. Pub. 201401700204, which is incorporated herein by reference.

In certain embodiments, the subject microdevices formed according to the methods of the present disclosure find use in influencing cellular behavior and development that are relevant for studying wound healing and stem cell development.

In certain embodiments, the subject microdevices formed according to the methods of the present disclosure find use in developing enhanced biological assays, such as diagnostic analyte detection assays. In addition to efficient loading, the concentration of luminescent samples to microscale regions may also increase local signal intensity, thereby enhancing sensitivity. Furthermore, based on a pore density of approximately $10^8$ pores/cm$^2$ for the 290 nm pore size AAO membranes, nanowires fabricated from these membranes to 15 µm in length and 320 nm in diameter will provide an approximately 1000-fold increase in surface area available for conjugation of biomolecules or reagents, also potentially enhancing signal intensity.

Kits

Also provided herein are kits containing a microdevice that includes a plurality of nanowires disposed on a biocompatible surface, wherein the biocompatible surface includes a first biocompatible polymeric layer and a plurality of nanowires formed from a second biocompatible polymeric layer disposed on a surface of the first biocompatible polymeric layer. In certain embodiments, the kit includes a substrate, such as a silicon substrate. Thus, in certain embodiments, the kit provides the microdevices disposed on a substrate. In some instances, the microdevices in the kit are disposed on the substrate in an array. In some instances, the kit contains a microdevice containing a plurality of nanowires disposed on a biocompatible surface, wherein the biocompatible surface includes a first biocompatible polymeric layer and a plurality of nanowires formed from a second biocompatible polymeric layer disposed on a surface of the first biocompatible polymeric layer, and wherein an active agent is disposed on the plurality of nanowires. In certain embodiments, the kit contains sterilized microdevices.

Components of a subject kit can be in separate containers; or can be combined in a single container, where desired.

In addition to the above-mentioned components, a subject kit can further include instructions for using the components of the kit and to practice the subject methods of delivering an active agent to a mucosal surface. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, flash drive, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1: Fabrication of Micropatterned Nanowire Arrays

An approach to fabricate polymeric nanowire arrays with custom micropatterns and tunable nanowire dimensions was developed. Two variations of this approach were utilized to pattern nanowire arrays either over a flat polymer base layer or on the surface of detachable microstructures. The ability of these micropatterned nanowire arrays to 1) provide efficient drug/reagent loading with micron-scale resolution and 2) influence cellular behavior through both micro- and nanoscale interactions was investigated.

The fabrication approach employed polymer templating, a rapid and inexpensive nanofabrication technique that involved extruding a polymer into a nanoporous membrane and subsequently etching the membrane to expose polymeric nanowires. For custom nanowire array micropatterning and enhanced resolution, templating and photolithographic techniques were combined. As shown in FIG. 1, two approaches were used to fabricate either flat or elevated nanowire arrays consisting of a polymethyl methacrylate (PMMA) base layer coated with polycaprolactone (PCL) nanowires. PMMA is a common material in FDA-approved orthopedic implants, and PCL is a polymer used in FDA-approved sutures and drug delivery devices and has been shown to facilitate cellular adhesion and growth.

FIG. 1. Fabrication approaches to create flat and elevated PCL nanowire arrays. A. Flat nanowire array fabrication. (i) A nanoporous AAO membrane was coated with positive photoresist (red) and patterned by exposure to UV light through a computer-designed photomask with subsequent chemical development. (ii) The AAO membrane was inverted, and its micropatterned side was brought into contact with a layer of PCL (white) deposited over a PMMA base layer (gray) under heat, allowing PCL to melt and extrude into membrane pores in regions not coated with photoresist. (iii) The AAO and resist were dissolved in an alkaline solution to expose the PCL nanowires. B. Elevated nanowire array fabrication. (i) A layer of PMMA (gray) spun-cast onto a silicon wafer (black) was coated with positive photoresist (red), which is patterned via photolithography. (ii) The photoresist pattern was transferred to the PMMA layer by reactive ion etching with oxygen plasma. (iii) After stripping the photoresist, the PMMA features were heated and brought into contact with PCL (white) spun-cast onto a separate silicon wafer. (iv) Upon separation of the wafers, the PCL lifted off onto the PMMA features. (v) The PCL was melted and templated with an AAO membrane. (vi) The AAO membrane was etched in an alkaline solution.

To form flat PCL nanowire microarrays (FIG. 1A), a nanoporous anodized aluminum oxide (AAO) membrane (GE Healthcare, Piscataway, N.J.) was spun-cast with Microposit 81818 positive photoresist (MicroChem, Westborough, Mass.) and patterned via photolithography with grooves of 10, 20, 40, or 80 μm widths and equal spacing. The patterned side of the AAO membrane was then brought into contact with a wafer spun-cast with a PMMA base layer and an overlying layer of PCL 5, 10, or 15 μm in thickness and heated to 80° C., above the melting temperature of PCL but below that of PMMA. After uptake of melted PCL into pores of the AAO membrane in regions not coated with photoresist, the AAO membrane and photoresist were selectively dissolved in a 0.5 M sodium hydroxide solution for 1 h to expose the PCL nanowires.

To form elevated nanowire microarrays (FIG. 1B), PMMA and an overlying photoresist layer were spun-cast onto a silicon wafer, and the photoresist was patterned with arrays of squares with 10, 20, 40, or 80 μm edge lengths and equal spacing via photolithography. The photoresist pattern was then transferred to the PMMA layer by reactive ion etching with oxygen plasma to form elevated PMMA structures. After chemically stripping the remaining photoresist, the PMMA features were heated to 80° C. and brought into contact with PCL spun-cast onto a separate wafer at thicknesses of 5, 10, or 15 μm. Upon separation of the wafers, the PCL lifted off onto the PMMA features. Finally, the PCL-coated features were templated with an AAO membrane at 80° C., and the membrane was etched in 0.5 M sodium hydroxide for 1 h.

These fabrication approaches resulted in micropatterned arrays of densely packed PCL nanowires on either flat or elevated PMMA base layers (FIG. 2). Fabrication approaches for both flat and elevated nanowire arrays had adequate resolution for all feature sizes tested (10 to 80 μm). Nanowires formed clusters approximately 1 to 10 μm in width, possibly as a result of capillary force during drying in preparation for SEM. The flat nanowire arrays had well-defined borders, but the elevated nanowire arrays had rounded corners and edges overhanging the PMMA base layer (FIGS. 2 and 3A), likely due to beading of molten PCL during the lift-off step and/or compression during templating.

FIG. 2. Nanowire array fabrication approaches demonstrated sufficient resolution to pattern features as small as 10 μm. SEM micrographs of flat (A-D) and elevated (E-H) arrays of 10 μm (A, E), 20 μm (B, F), 40 μm (C, G), and 80 μm (D, H) feature sizes. Scale bars are 20 μm.

Figure 3:
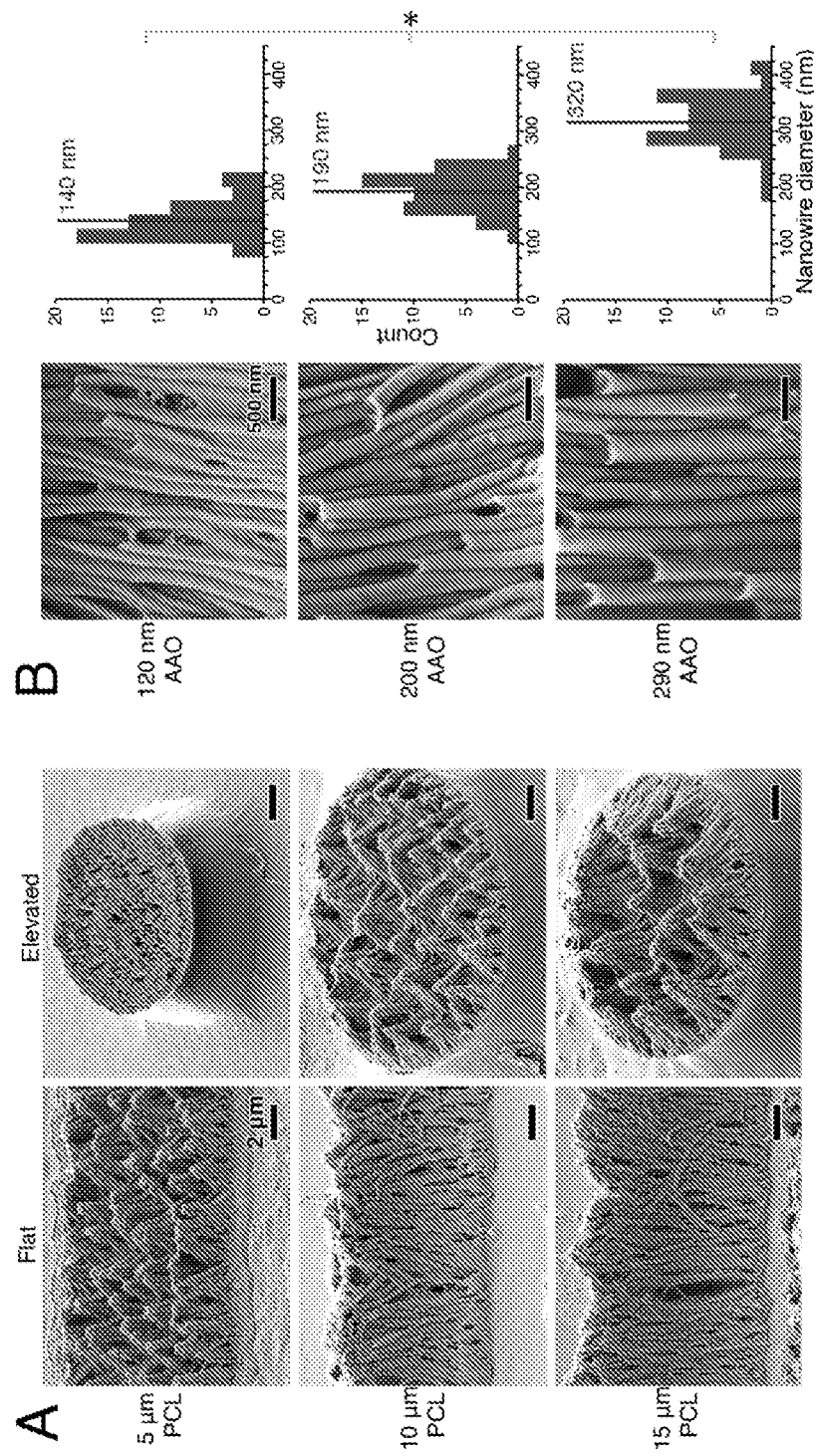
FIG. 3 shows SEM micrographs and measurements of nanowires formed on microdevices, according to embodiments of the present disclosure.

FIG. 3. Adjusting templating parameters to tune nanowire dimensions. A. PCL thickness controlled nanowire length. 45° SEM micrographs of flat and elevated nanowire arrays fabricated with PCL thicknesses of 5, 10, and 15 μm demonstrated that nanowire length increases with PCL thickness. Scale bars are 2 μm. B. Membrane pore size controlled nanowire diameter. As shown in SEM micrographs and histograms, nanowire diameters correlated with AAO membrane diameter. Templating with mean membrane pore diameters of 120±40, 200±60, and 290±50 nm yielded mean nanowire diameters of 140±30, 190±30, and 320±50 nm, respectively. Scale bars are 500 nm. *Indicates statistically significant difference between average nanowire diameter with $p<0.001$.

After demonstrating custom patterning of nanowire arrays, approaches to tune nanowire dimensions were investigated. First an approach to adjust nanowire length was investigated. For the approach used in this study, it was hypothesized that templating would occur until the AAO membrane contacted the PMMA base layer, allowing for control of nanowire length by adjusting PCL thickness. For flat arrays, nanowire lengths roughly matched respective PCL thicknesses for PCL layers 5, 10, and 15 μm thick (FIG. 3 A). Nanowires of the elevated arrays also scaled in length with PCL thickness but were shorter than nanowires of flat arrays fabricated with identical PCL thicknesses, indicating only partial adhesion of the PCL layer during the lift-off step. Control over nanowire diameter through selection of AAO membranes of varying pore sizes was also investigated. As shown in FIG. 3 B, templating with AAO membranes with mean pore sizes of 120±40, 200±60, and 290±50 nm (FIG. 4) resulted in mean nanowire diameters of 140±30, 190±30, and 320±50 nm, respectively. Thus, in addition to customizable nanowire array patterning, nanowire dimensions can also be tuned for length and diameter by adjusting PCL thickness and AAO pore size, respectively.

Figure 4:
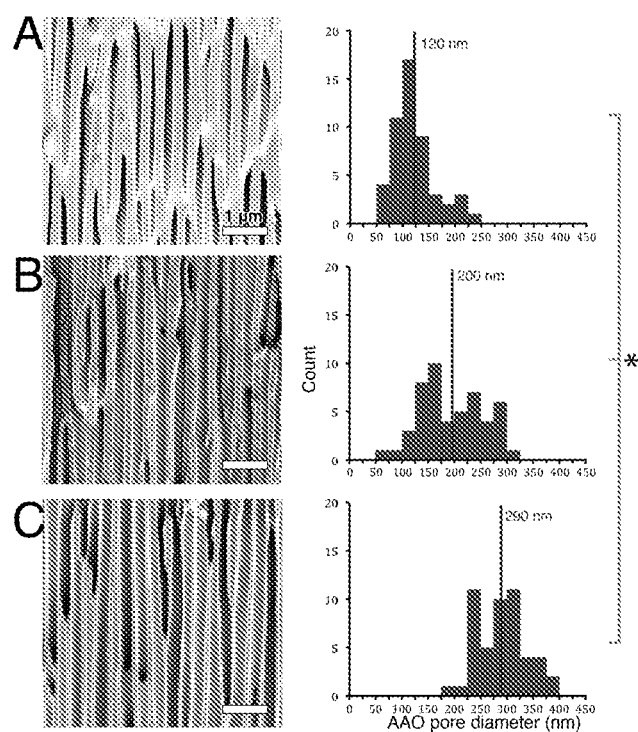
FIG. 4 shows further SEM micrographs and measurements of nanowires formed on microdevices, according to embodiments of the present disclosure. Cross sections of Whatman Anodise® AAO membranes with nominal pore diameters of 0.02 µm (A), 0.1 (B), and 0.2 µm (C) were imaged with SEM, and diameters were measured to determine average pore diameters of 120±40, 200±60, and 290±50 nm, respectively. Scale bars are 1 µm. *Indicates statistically significant difference between average nanowire diameter with $p<0.001$.

FIG. 4. SEM images and histograms of AAO pore diameters. Cross sections of Whatman Anodise® AAO membranes marketed as 0.02 μm (A), 0.1 μm (B), and 0.2 μm (C) pore sizes were imaged with SEM, and diameters were measured to determine average pore diameters of 120±40, 200±60, and 290±50 nm, respectively. Scale bars are 1 μm. *Indicates statistically significant difference between average nanowire diameter with $p<0.001$.

Example 2: Loading Nanowire-Coated Microdevices with Active Agent

It was hypothesized that the increased surface area of the nanowire regions of micropatterned arrays would facilitate high-resolution drug and reagent loading via capillary action. To investigate this loading approach, elevated 40 μm features with either PCL nanowires or non-templated PCL (termed "flat PCL") as a control were wetted with solutions of FITC-BSA in water or Oregon Green 488 paclitaxel in ethanol at 5 μg/cm$^2$, inverted, and allowed to dry. The features were then imaged with confocal microscopy to determine the localization of the fluorescently labeled paclitaxel and BSA. While features with flat PCL demonstrated loading at the base of the elevated structures (FIG. 5 A,D), features coated with PCL nanowires facilitated loading onto the elevated surface of the structures (FIG. 5 B,E) indicating that the nanowire arrays mediated drug/reagent loading. Within the nanowire arrays, the FITC-BSA and Oregon Green 488 paclitaxel intensity patterns showed clustered regions approximately 1 to 10 μm in width (FIG. 5 C,F), similar to the PCL nanowire folding/clustering pattern observed in nanowire arrays (FIGS. 2 and 3). This intensity pattern indicated that drug/reagent localized to clustered nanowires, suggesting that loading was mediated by capillary action between nanowires as solvent evaporated. While many drug loading techniques are only compatible with water-soluble drugs, micropatterned nanowire arrays provided efficient loading of both the water-soluble protein FITC-BSA and the hydrophobic, water-insoluble drug Oregon Green 488 paclitaxel through selection of solvents to maximize solubility. Drug loading efficiencies of nanowire arrays, which were calculated from averaged confocal imaging Z-stacks as the ratio of fluorescence intensity integrated over micropatterned regions to fluorescence intensity integrated over the entire analyzed region, were 94% for Oregon Green 488 paclitaxel and 88 2% for FITC-BSA (FIG. 5 G). Further investigation of FITC-BSA loading demonstrated efficient localization onto both flat and elevated nanowire arrays for all feature sizes tested (FIG. 6).

FIG. 5. Nanowires mediate drug/reagent loading. Three-dimensional confocal imaging reconstructions of 5 µg/cm$^2$ Oregon Green 488 paclitaxel (A-B) and FITC-BSA (D-E) loaded onto features with either flat PCL (A, D) or PCL nanowires (B, E) demonstrated that nanowires dramatically enhance drug/reagent localization to array features. Two-dimensional confocal imaging slices of loaded nanowire arrays (C, F) show clustered localization upon loading, suggesting that loading occurs between nanowires as a result of capillary action. G. Loading efficiencies were quantified by analysis of fluorescence intensity. All scale bars are 20 µm.

FIG. 6. Nanowires provide efficient, high-resolution loading of BSA-FITC for flat and elevated features. Fluorescent images of flat (A-D) and elevated (E-H) nanowire arrays of 10 µm (A, E), 20 µm (B, F), 40 µm (C, G), and 80 µm (D, H) feature sizes loaded with BSA-FITC at 5 µg/cm$^2$ showed efficient loading for all feature sizes tested. Scale bars are 50 µm.

The ability to concentrate reagents onto high-resolution patterns could be employed to enhance biological analysis. For example, this approach could be utilized to miniaturize biological assays into a microarray format while providing high-throughput, low-waste loading of reagents or samples. In addition to efficient loading, the concentration of luminescent samples to microscale regions may also increase local signal intensity, thereby enhancing sensitivity. Furthermore, based on a pore density of approximately 10$^8$ pores/cm$^2$ for the 290 nm pore size AAO membranes, 46 nanowires fabricated from these membranes to 15 µm in length and 320 nm in diameter will provide an approximately 1000-fold increase in surface area available for conjugation of biomolecules or reagents, also potentially enhancing signal intensity.

This loading approach may also have applications to biomedical microdevice technology. Microfabricated devices loaded with drug can significantly increase the uptake of drug in vitro and in vivo. Here, an example of polymeric, nanowire-coated microparticles was presented and an inherent mechanism for high-throughput, low-waste drug loading was demonstrated. These microparticles were detachable from the silicon wafer (FIG. 7) and were similar in geometry to previously developed microfabricated devices for enhanced drug uptake. Specifically, they were planar in shape with a drug reservoir on only one side of the device, features shown to facilitate adhesion to monolayers of epithelial cells and unidirectional drug release toward epithelial tissue. The nanowire coating may provide additional advantages, as nanowires are capable of interacting with epithelial layers to increase cytoadhesion and interrupting cell-cell junctions to enhance epithelial permeability.

Figure 7:
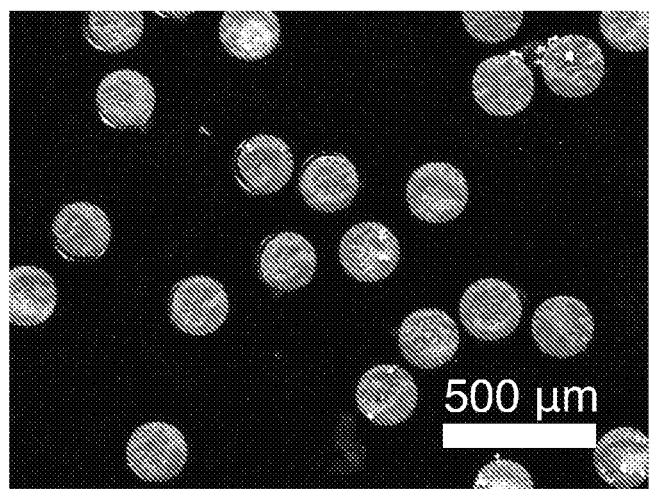
FIG. 7 shows a brightfield image of detached microdevices, according to embodiments of the present disclosure.

FIG. 7. Elevated nanowire-coated microparticles were detachable. A brightfield image of elevated nanowire coated microparticles following detachment by scraping the silicon wafer with a razor.

Example 3: Hierarchical Topographical Influence of Nanowire-Coated Microdevices on Cellular Behavior The application of micropatterned nanowire arrays to provide hierarchical topographical control over cellular behavior was investigated. Microscale topography influences cell growth through the alignment of cells with topographical features, a cellular behavior known as contact guidance. This influence over cellular shape and elongation can alter cytoskeletal tension, resulting in altered signal transduction. Nanoscale features, which approach the macro-molecular scale, interact more directly with integrins, transmembrane receptors that allow cells to recognize and bind to their external environment, leading to the formation of focal adhesion complexes. Both the nanoscale distribution of integrin receptors and the micron-scale size and shape of focal adhesions influence cellular behavior through downstream signaling pathways. In vivo, cells reside in niche environments with tissue-specific micro- and nano-topography. Skin, bone, tendon, neural tissues, skeletal muscle, and blood vessels all present hierarchical micro/nanostructures of specific dimensions. Scaffolds designed to mimic the micro- and nanotopography of cellular niche environments have been used to decrease fibrosis and enhance regeneration for wound healing, maintain stem cell pluripotency in vitro, and direct stem cell growth and differentiation for therapeutic applications.

Figure 8:
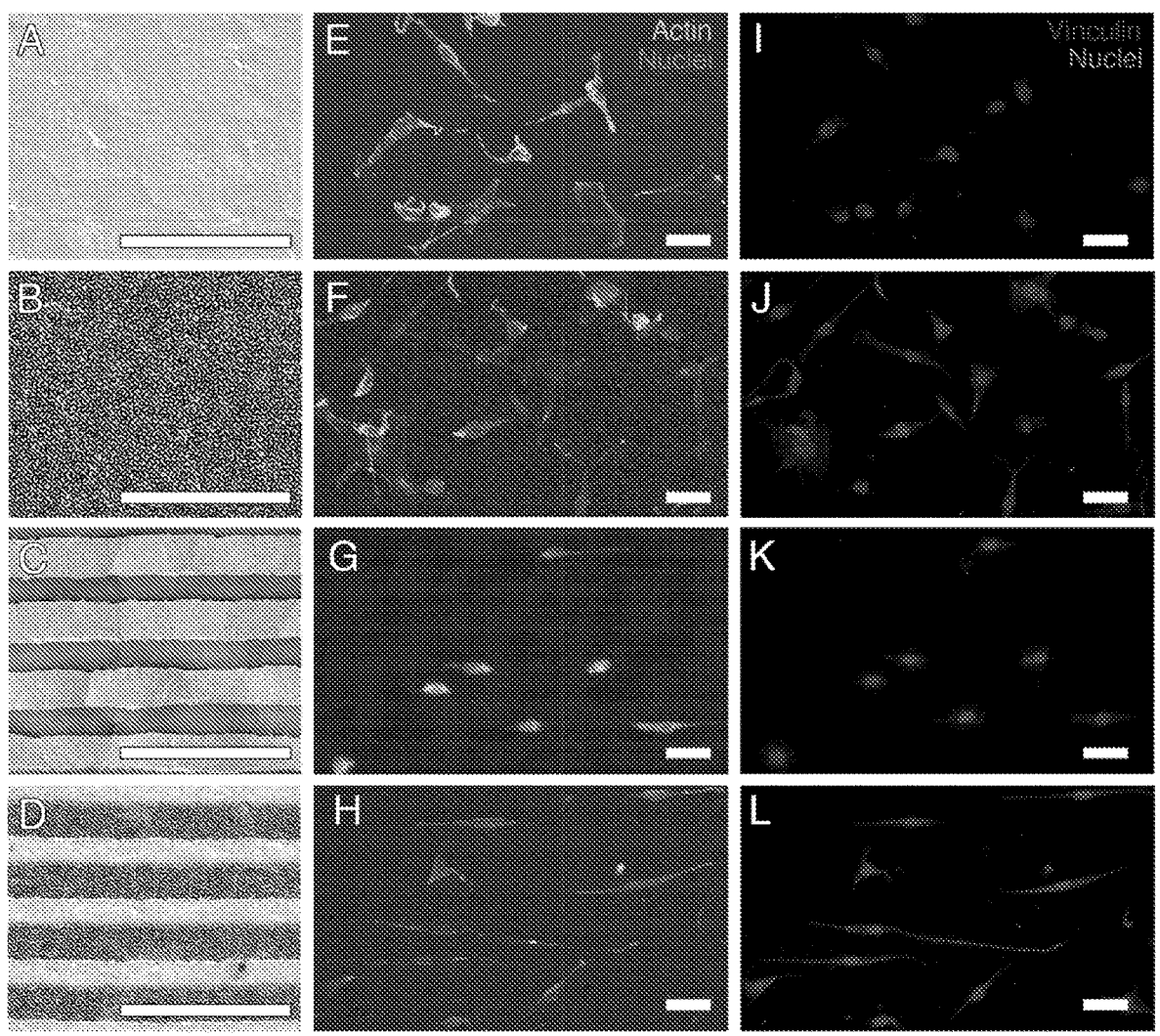
FIG. 8 shows scanning electron microscopy micrographs of microdevices with and without a nanowire-coated surface, and fluorescent images of fibroblasts cultured on the microdevices, according to embodiments of the present disclosure.

To investigate the ability of micropatterned nanowire arrays to simultaneously influence cells on both the microscale and nanoscale, 3T3 fibroblast cells were grown on scaffolds consisting of flat PCL, PCL nanowires, micropatterned flat PCL (with grooves 10 µm in width and 5 µm in height), and micropatterned nanowire arrays (with grooves 10 µm in width and nanowires 5 µm in length) (FIG. 8 A-D). After two days of culture, fibroblasts were fixed, permeabilized, and stained to visualize nuclei, actin, and vinculin, a focal adhesion protein (FIG. 8 E-L). While fibroblasts cultured on arrays without micropatterns showed isotropic morphology as indicated by actin staining (FIG. 8 E-F), fibroblasts cultured on micropatterned scaffolds extended along the scaffold grooves (FIG. 8 G-H). However, fibroblasts cultured on micropatterned nanowires showed a significantly higher degree of elongation than cells cultured on flat PCL microgrooves lacking nanotopography. Vinculin staining, which visualized the effects of scaffold topography on cellular focal adhesion formation, provided a possible explanation for this enhanced cellular elongation. The extensions of cells grown on nanowire arrays (FIG. 8 J,L) showed increased vinculin localization relative to cells grown on scaffolds lacking nanotopography (FIG. 8 I,K). This observation suggested that nanowires enhanced focal adhesion formation, which agrees with previous studies demonstrating that polymeric nanowire membranes promote cellular adhesion.

FIG. 8. Micropatterned nanowire arrays simultaneously influence cellular behavior on both the micro- and nanoscales. Fibroblasts were cultured on flat PCL (A), PCL nanowire (B), micropatterned flat PCL (C), and micropatterned PCL nanowire (D) scaffolds (imaged with SEM). Staining of actin (green) and nuclei (blue) merged with brightfield scaffold images (E-H) demonstrated that micropatterned scaffolds (G-H) promote cellular alignment to scaffold grooves, with micropatterned nanowires (H) providing enhanced cellular elongation relative to micropatterned flat PCL (G). Vinculin (red) and nuclei (blue) staining (I-L) demonstrated that nanowire scaffolds increased vinculin localization to cellular extensions (J, L) relative to cells cultured on flat PCL scaffolds (I, K), indicating that nanowires enhanced focal adhesion formation. Scale bars are 50 μm.

Taken together, these results demonstrate that the micropatterned nanowire arrays influenced cells through both microgroove-mediated contact guidance and nanowire-mediated focal adhesion formation to provide a unique cellular morphology not achievable through micro- or nanotopographies alone. With customizable micropatterning and tunable nanowire length and diameter, this fabrication approach could be used to create scaffolds designed to mimic different cellular niche environments with specific nanoscale topographies and microscale patterns. As PCL can be functionalized and matrix-loaded with chemical factors, signaling molecules may also be incorporated into these scaffolds to further recapitulate cellular niche environments.

Example 4: Nanowire-Coated Microdevice Fabrication

Another example of fabricating a nanowire-coated microdevice is shown in FIG. 9.

FIG. 9. A. 1) PMMA ($2^{nd}$ layer from the bottom) 2) PVA ($3^{rd}$ layer from the bottom) 3) SU-8 ($4^{th}$ layer from the bottom) were spin cast onto a silicon wafer (bottom most layer). B. SU-8 was selectively crosslinked by exposure through a photomask. C. Reactive ion etching with oxygen plasma was performed for pattern transfer to PVA and PMMA layers. D. Dissolution of sacrificial PVA layer in water released overlying SU-8. E. Microdevices were brought into contact with PCL (gray) spin-cast onto a second wafer (black) at 80° C. PCL-PMMA devices (F) were then templated with a nanoporous aluminum oxide membrane at 80° C. (G), which was subsequently dissolved in 1 M NaOH, leaving nanowire-coated microdevices (H). I. Microdevices were loaded with drug by capillary action during solvent evaporation.

Example 5: Enhanced Microdevice Cytoadhesion

Figure 11:
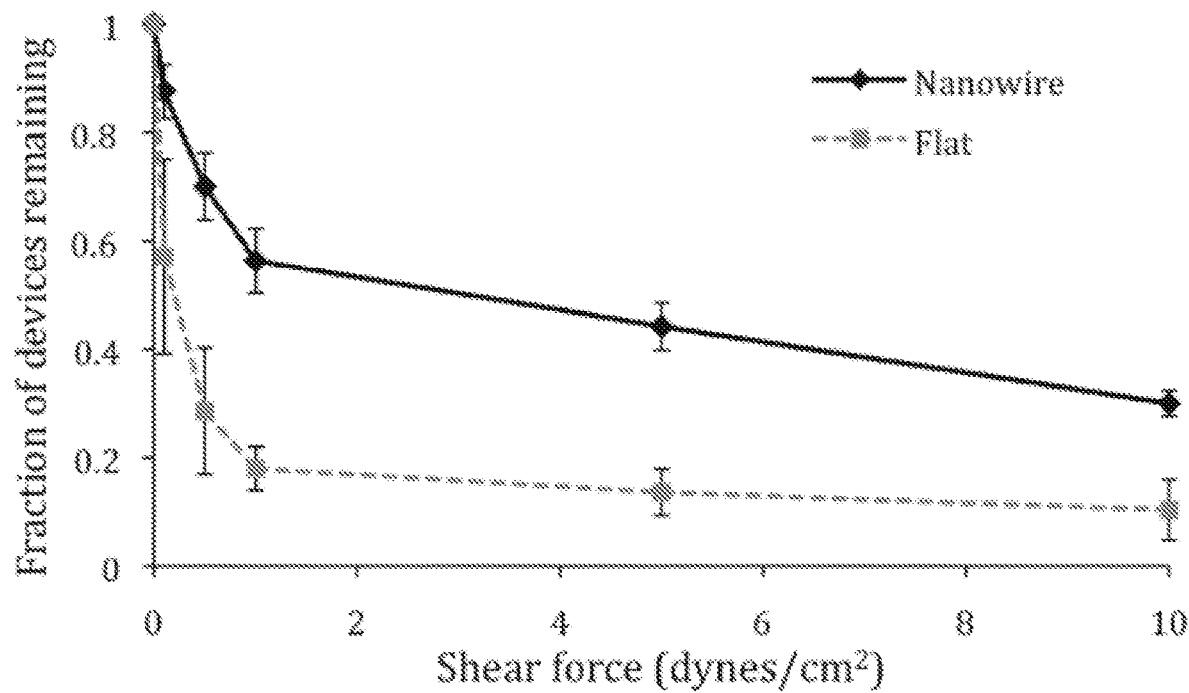
FIG. 11 shows enhanced cytoadhesion of nanowire-coated microdevices, according to embodiments of the present disclosure.

Nanowires enhanced microdevice cytoadhesion (FIG. 11). Devices with flat and nanowire surfaces were incubated on a layer of Caco-2 cells for 10 min before exposure to increasing shear forces at 5 min. intervals, and the fraction of devices remaining after exposure to each shear force was determined.

Example 6: Enhanced Epithelial Permeation of Protein

Figure 12:
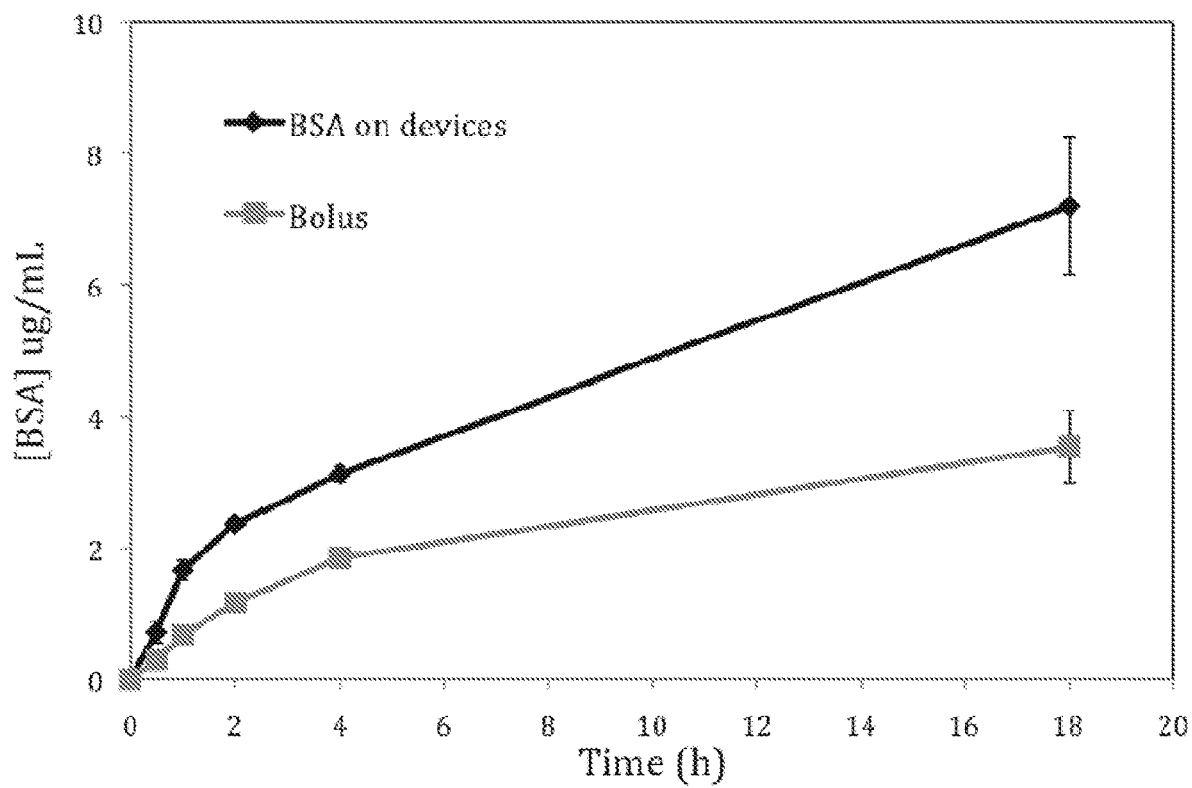
FIG. 12 shows enhanced epithelial penetration of protein using nanowire-coated microdevices, according to embodiments of the present disclosure.
Figure 13:
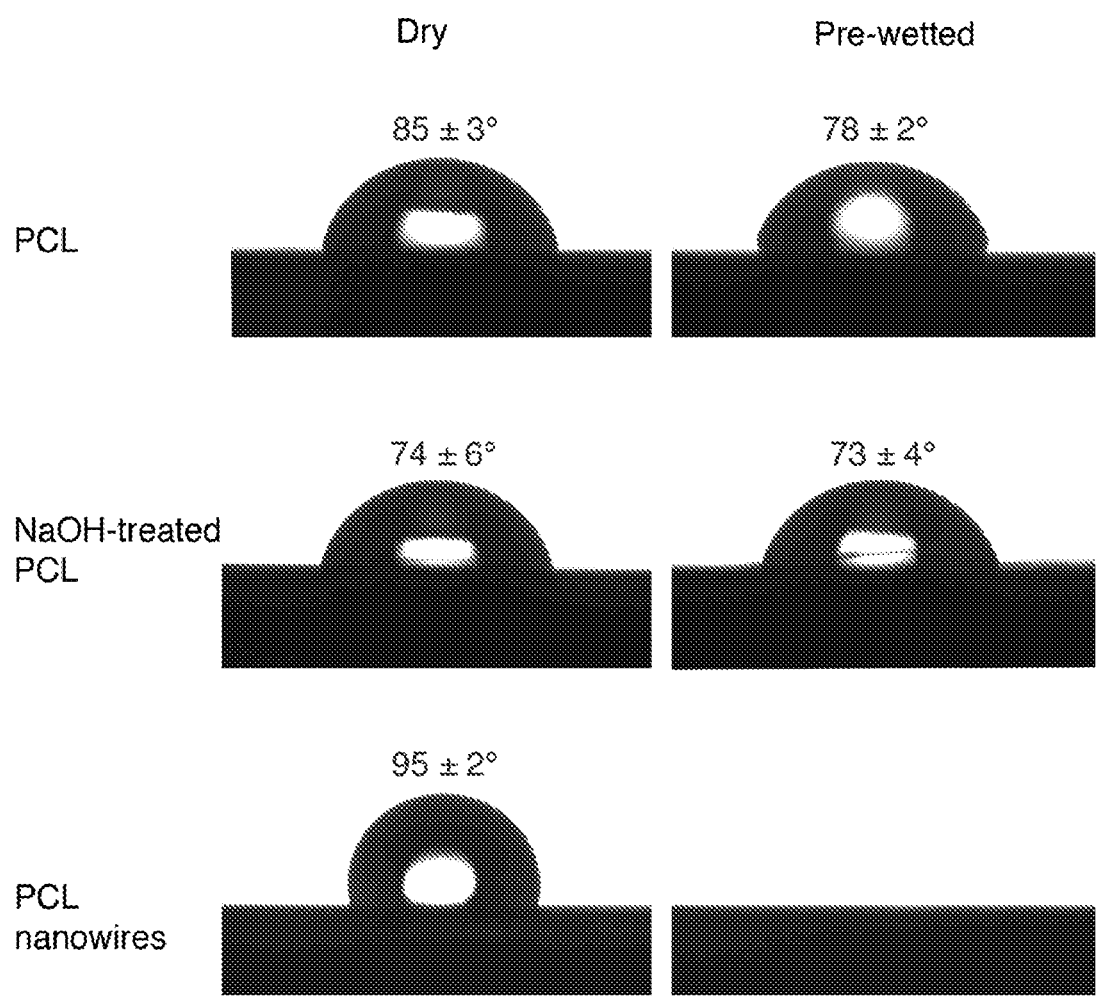
FIG. 13 shows that nanowire films are highly wettable following initial contact with water. 5 µL water were dispensed onto PCL films composed of PCL, PCL treated with 0.5 M NaOH for 1 h (to match NaOH treatment for AAO membrane etching), and PCL nanowires with and without pre-wetting. Pre-wetting consisted of submerging the films in water, spinning the films at 2000 rpm for 5 s to remove excess water, and imaging droplets within 1 min. Under dry conditions, the nanowire coating resulted in a higher contact angle than both non-templated PCL and NaOH-treated non-templated PCL, possibly as a result of air entrapment within the nanowire arrays. However, when nanowire films were pre-wetted, water droplets were taken up by the nanowire arrays, preventing measurement of contact angle and demonstrating that nanowires arrays are highly wettable following initial exposure to water.

Nanowire-coated microdevices enhanced epithelial permeation of protein (FIG. 12). BSA loaded onto nanowire-coated microdevices or as a bolus dose was added to the apical chamber of a transwell insert with a monolayer of Caco-2 cells, and the mass of BSA permeating through the Caco-2 cell monolayer to the basolateral chamber was measured over 18 hours.

Materials and Methods
Micropatterned Nanowire Array Fabrication

Micropatterned PCL nanowire arrays on PMMA were fabricated by spin-coating a nanoporous AAO membrane (GE Healthcare, Piscataway, N.J.) with Microposit S1818 positive photoresist (MicroChem, Westborough, Mass.) at 2500 rpm for 30 s with a ramp speed of 1000 rpm/s. The photoresist was baked at 110° C. for 1 min. and allowed to cool. The photoresist was then exposed to 225 mJ/cm2 of 405 nm UV light through a computer-designed photomask with grooves with 10, 20, 40, or 80 μm widths and equal spacing or other various micropatterns. The micropatterned AAO membrane was then submerged in 351 Developer (MicroChem) for 1 min. with gentle shaking, rinsed with dH2O, and allowed to dry. Separately, a silicon wafer was coated with a 110 mg/mL solution of 950 kDa PMMA in anisole (MicroChem) at 350 rpm for 15 s followed by 1400 rpm for 30 s and baked at 110° C. for 1 min. The resulting 5 μm PMMA base layer was coated with an overlying layer of PCL (Mn=80 kDa, Sigma-Aldrich) 5, 10, or 15 μm in thickness. The 5, 10, and 15 μm PCL layers were obtained by spin-coating 50 to 150 mg/mL PCL in 2,2,2-trifluoroethanol (TFE) at 1000 to 2000 rpm for 30 s following a pre-spin at 500 rpm for 10 s. The PCL was then brought into contact with the micropatterned side of the AAO membrane and heated to 80° C. for 5 min. After uptake of melted PCL into pores of the AAO membrane in regions not coated with photoresist, the AAO membrane and photoresist were selectively dissolved in 0.5 M NaOH for 1 h to expose the PCL nanowires. Finally, the features were rinsed 5 times with dH2O. For cell culture experiments, the film was peeled from the silicon wafer prior to sterilization.

To fabricate nanowire arrays on discrete PMMA microstructures, a 110 mg/mL solution of 950 kDa PMMA in anisole (MicroChem) was spin-coated onto a silicon wafer at 350 rpm for 15 s followed by 1400 rpm for 30 s and baked at 110° C. for 1 min. The PMMA layer was coated with Microposit S1818 positive photoresist at 500 rpm for 10 s followed by 2500 rpm for 30 s and baked at 110° C. for 1 min. The photoresist was then exposed to 225 mJ/cm2 of 405 nm UV light through a computer-designed photomask with arrays of opaque squares with 10, 20, 40, or 80 μm edge lengths and equal spacing or other various micropatterns. The wafers were then submerged in 351 Developer for 1 min. with gentle shaking, rinsed with IPA, and dried with nitrogen. The photoresist pattern was then transferred to the PMMA layer by reactive ion etching with oxygen plasma (450 W, 200 mTorr, 6.5 min.) to form PMMA microstructures. The remaining photoresist was stripped with Microposit Remover 1112A (MicroChem) for 1 min. under gentle shaking. The PMMA features were then heated to 80° C. and brought into contact with PCL spun-cast onto a separate wafer at thicknesses of 5, 10, or 15 μm, and the wafers were separated. The PCL-coated features were templated with an AAO membrane at 80° C. for 5 min., and the membrane was subsequently etched in 0.5 M NaOH for 1 h. Finally, the features were washed 5 times with dH2O.

Non-Templated, Micropatterned PCL Film Fabrication

Figure 19:
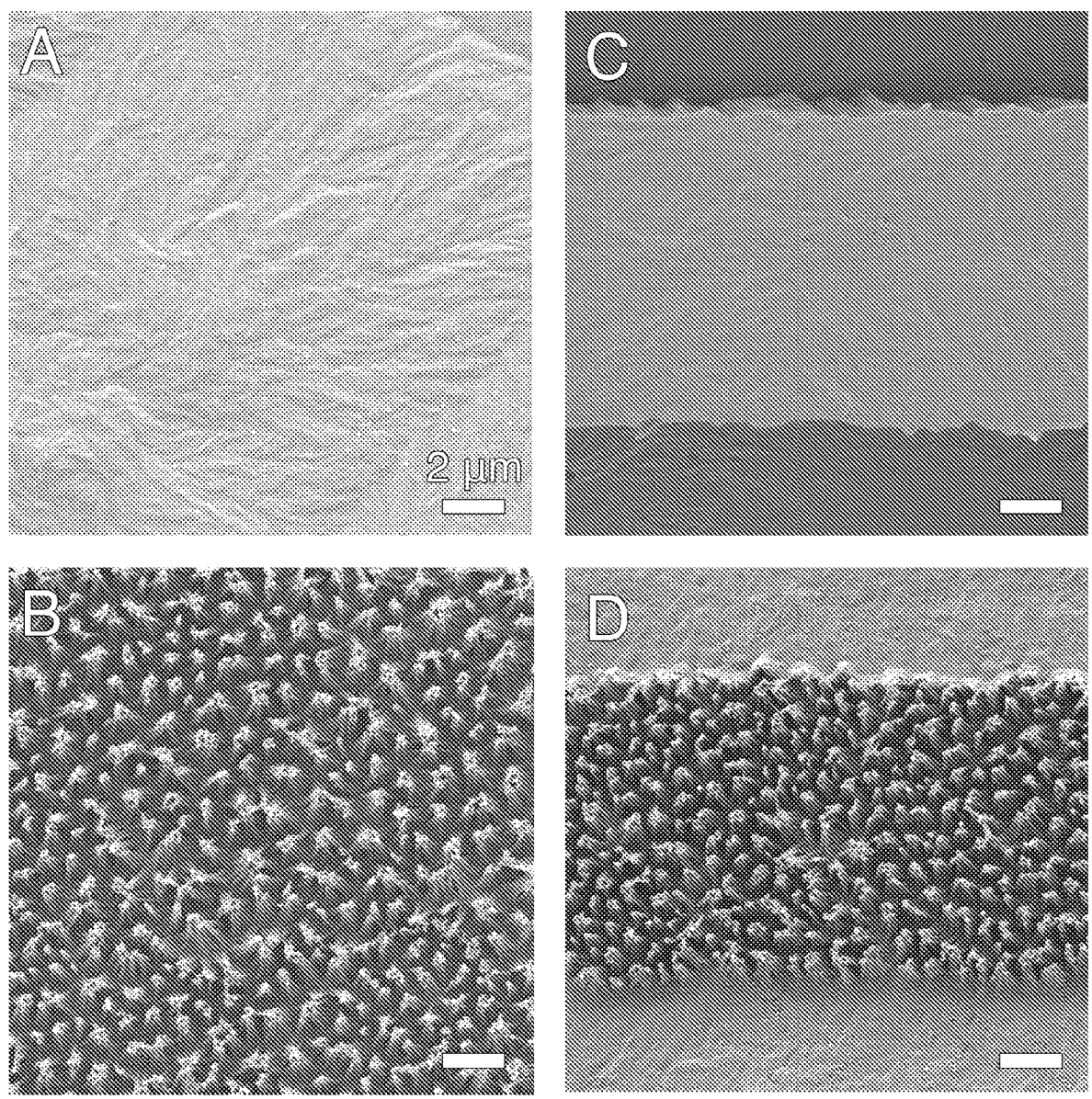
FIG. 19 shows high-resolution SEM micrographs of non-templated PCL (A), PCL nanowire (B), micropatterned non-templated PCL (C), and micropatterned nanowire (D) films used for fibroblast cell culture. Scale bars are 2 µm.

SU-8 2005 (MicroChem) was spun-cast onto a silicon wafer at 500 rpm for 10 s followed by 5000 rpm for 30 s and baked at 95° C. for 1 min. The SU-8 was then exposed to 365 nm UV light at 100 mJ/cm$^2$ through a photomask with 10 μm grooves with equal spacing and baked at 95° C. for 2 min. The wafer was developed in SU-8 Developer (MicroChem) for 1 min. under gentle shaking, rinsed with IPA, and dried with nitrogen. Sylgard 184 (Sigma-Aldrich) polydimethylsiloxane (PDMS) was mixed and de-gassed according to the manufacture's instructions and poured over the SU-8 mold. After de-gassing under vacuum for an additional 30 min., the PDMS was cured at 100° C. for 1 h, allowed to cool, and peeled from the SU-8 mold. A 100 mg/mL solution of 80 kDa PCL in TFE was then poured over the PDMS mold and allowed to cure overnight at room temperature. The PCL film was submerged in 200-proof ethanol, peeled from the PDMS mold, and treated with 0.5 M NaOH for 1 h prior to sterilization for cell culture. See FIG. 19.

Measurement of AAO Membrane Pore Diameter and Density and PCL Nanowire Diameter

Cross sections of Whatman Anodise® AAO membranes with nominal pore diameters of 0.02, 0.1, and 0.2 μm and nanowires resulting from templating PCL with these membranes were imaged with SEM, and the images were analyzed with ImageJ software to measure the average diameters of the AAO pores and PCL nanowires. 50 measurements were made for each sample. Pore density of AAO membranes with 200 nm nominal pore sizes were determined by imaging five 2 μm×2 μm regions of the AAO surface and counting the number of pores in each region, including overlapping pores on the bottom and left edges of the region and excluding overlapping pores on the right and top edges of the region. Mean values were reported with standard deviation.

Contact Angle Measurements

Contact angle measurements were performed with a Rame-Hart Standard Goniometer (Model 200-F4). 5 μL water were dispensed onto films with surfaces consisting of untemplated PCL, untemplated PCL treated with 0.5 M NaOH for 1 h (to match NaOH treatment for AAO membrane etching), and PCL nanowires with and without pre-wetting. Pre-wetting consisted of submerging the membranes in water for 1 min., spinning the films at 2000 rpm for 5 s to remove excess water, and imaging droplets within 1 min after spinning. Contact angles were measured on both sides of each droplet for 3 droplets per sample with DROPimage Standard software, and mean contact angles were reported with standard deviation.

Drug and Reagent Localization

Figure 14:
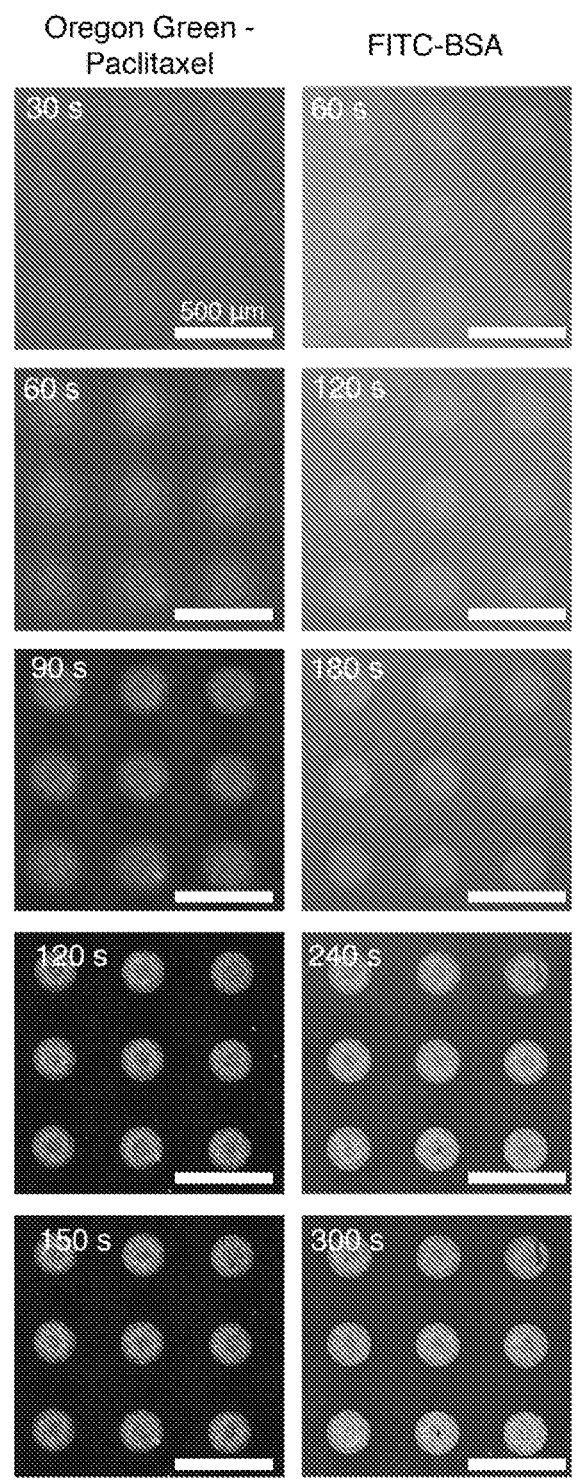
FIG. 14 shows time-lapse fluorescence imaging of Oregon Green Paclitaxel and FITC-BSA localization over micropatterned PCL nanowire array films demonstrates that drug/reagent solution collects over nanowire regions over time as solvent evaporates. Each image is labeled with the time after the addition of drug/reagent. Scale bars are 500 µm.
Figure 15:
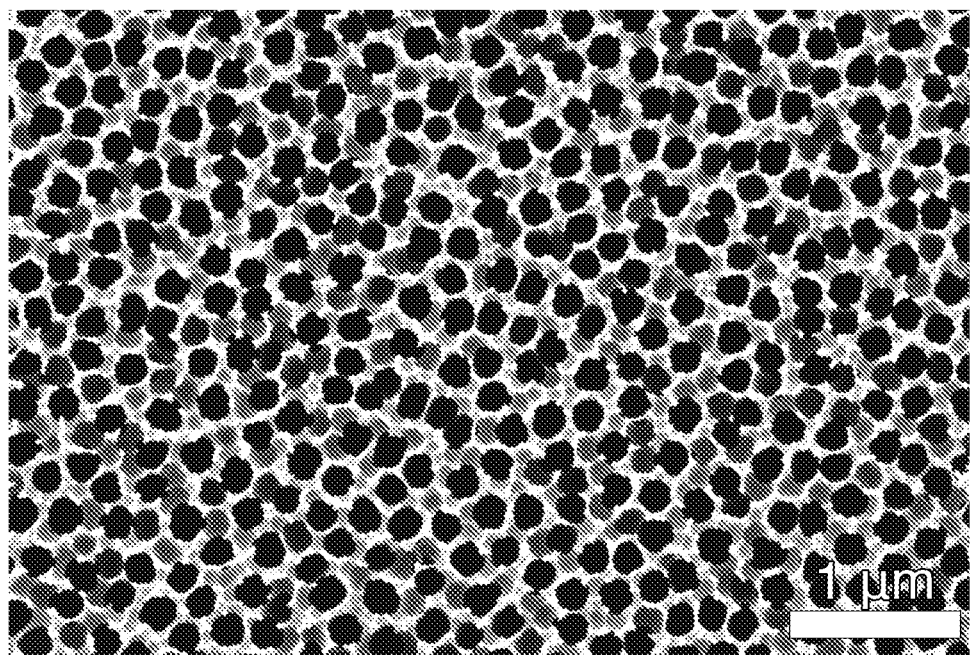
FIG. 15 shows SEM imaging and quantification of AAO membrane pore density. Five regions of 200 nm nominal pore size AAO membranes were analyzed to determine a density of 13±1.
Figure 16:
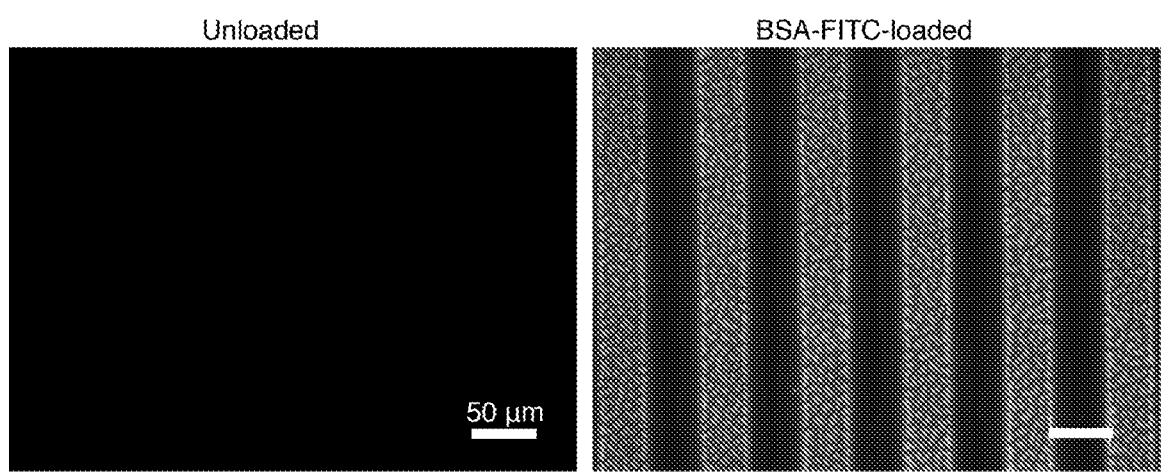
FIG. 16 shows that drug localization signal is not a result of polymer autofluorescence. Micro-grooved nanowire arrays on PMMA films show no detectable signal before loading but show localized signal under identical fluorescence imaging conditions after loading FITC-BSA at 5 µg/cm$^2$, indicating that observed signal is a result of FITC-BSA fluorescence rather than polymer autofluorescence. Scale bars are 50 µm.
Figure 17:
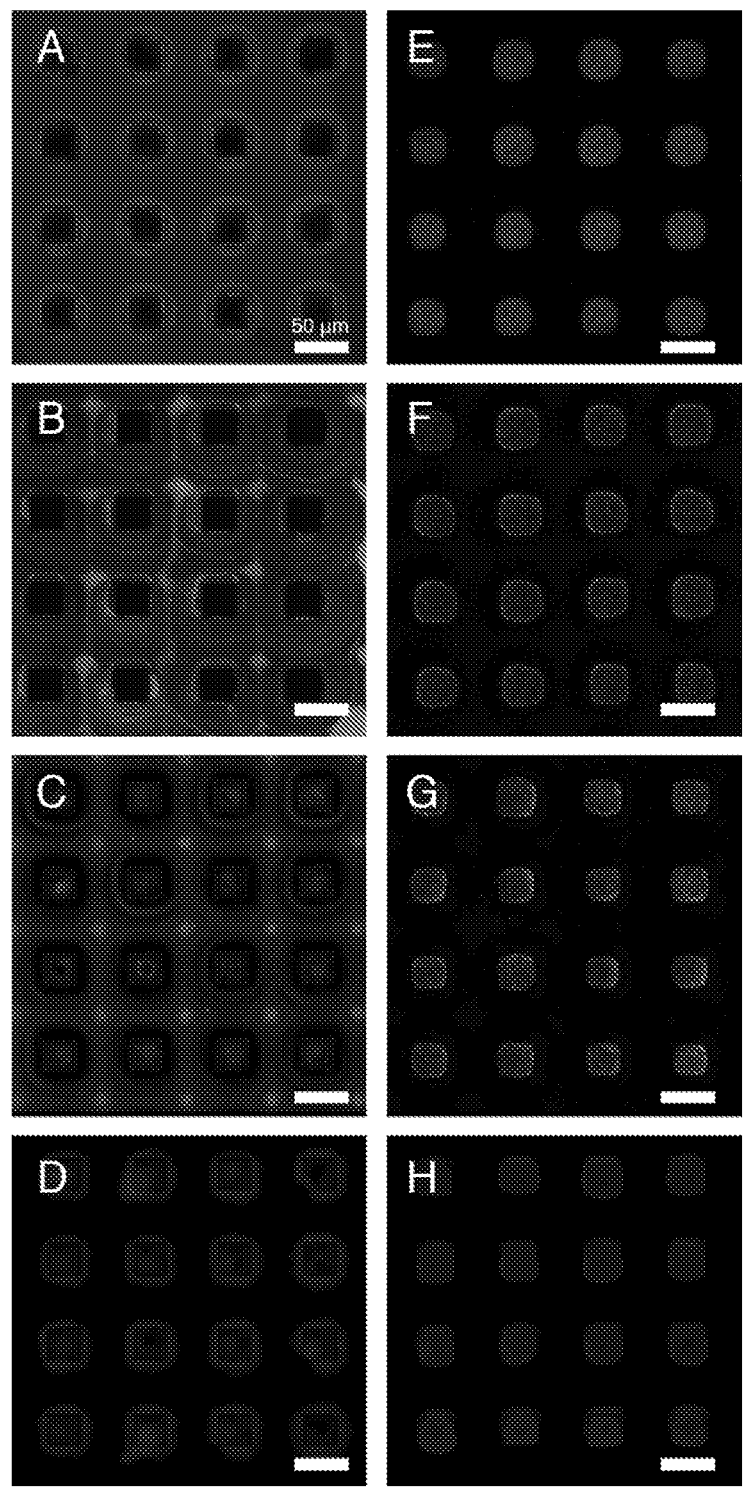
FIG. 17 shows Z-stacks of confocal fluorescent images of non-templated (A-D) and nanowire-coated (E-H) microstructures loaded with Oregon Green-paclitaxel (A, E), FITC-BSA (B, F), FITC-dextran (C, G), and Nile red (D, H) merged according to mean intensity values prior to quantification of fluorescence intensity to calculate localization efficiency. Scale bars are 50 µm.
Figure 18:
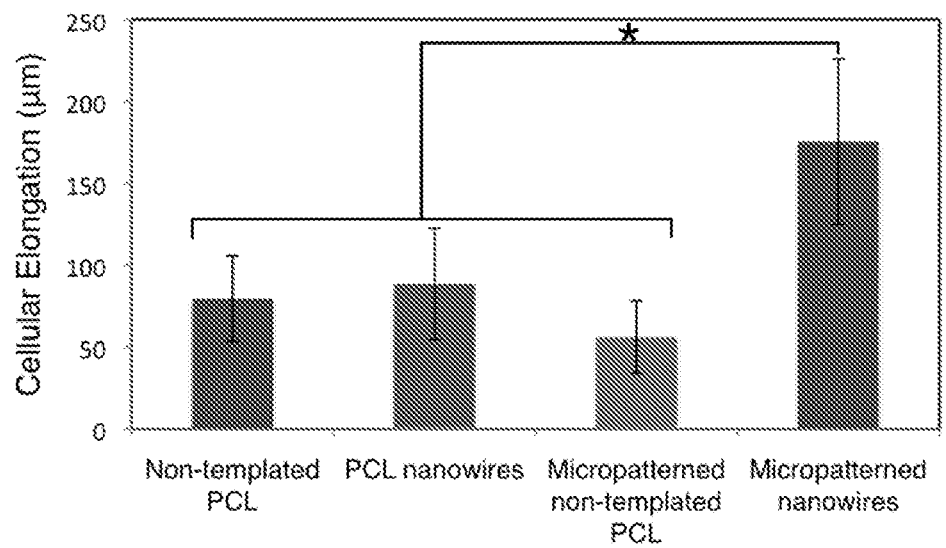
FIG. 18 shows quantification of cellular elongation and alignment of cells grown on PCL films. A. Quantification of cellular elongation, as determined by the distance between the two furthest points of each cell, demonstrated that cells grown on micropatterned nanowires were significantly more elongated than cells grown on films lacking micro- and/or nanotopography. *Indicates statistically significant difference between average cellular elongation with $p<0.01$. B. Quantification of cellular alignment demonstrated that micropatterned films enhanced cellular alignment in the direction of microgrooves.
Figure 18:
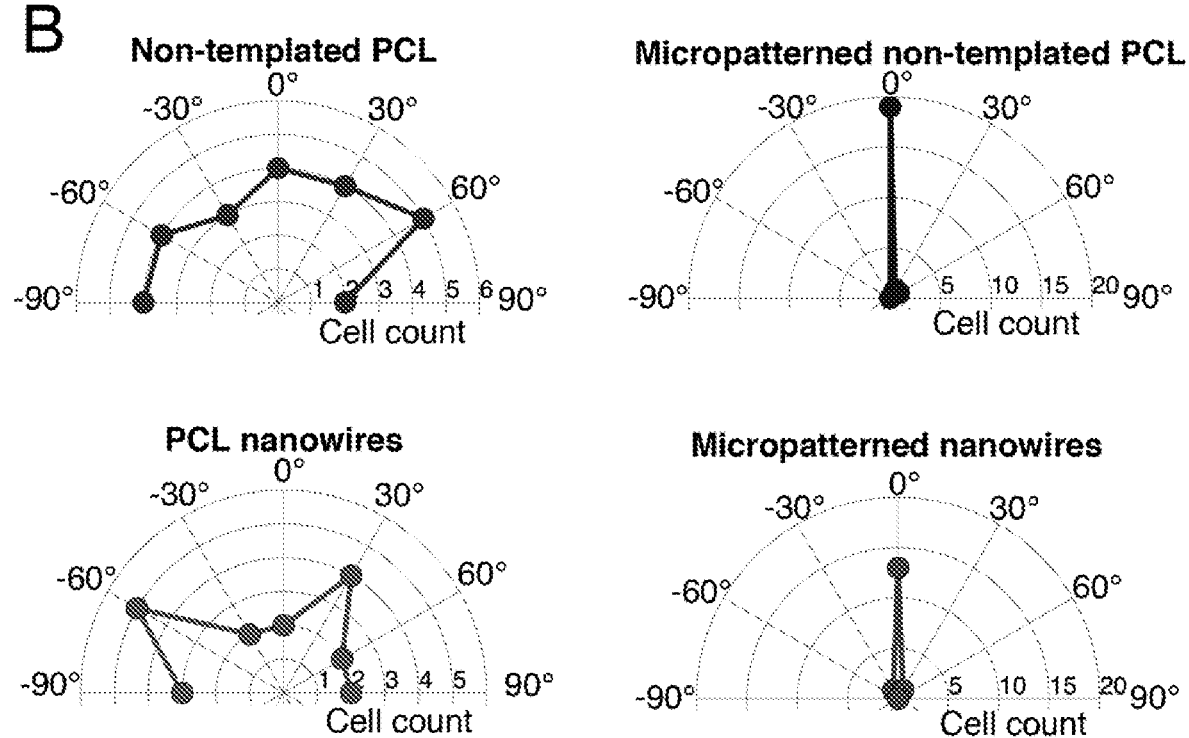

PMMA microstructures coated with either non-templated PCL or PCL nanowires were wetted with FITC-BSA and FITC-dextran (average MW=10 kDa) in dH$_2$O and Oregon Green paclitaxel and Nile red in ethanol at 5 μg/cm$^2$. The microstructures were then inverted and allowed to dry at room temperature. Arrays coated with non-templated PCL were fabricated in an identical manner to arrays coated with nanowires, except the templating step was omitted. PCL nanowire arrays on PMMA films were loaded in an identical manner to PMMA microstructures. All arrays used for drug localization were fabricated using PCL thicknesses of 10 μm. Z-stacks of drug/reagent-loaded features were captured at 1 μm intervals, capturing the entire microarray structures and wafer base layer, with a spectral confocal microscope (FIGS. 4, 17). Drug/reagent localization was also observed with a conventional fluorescence microscope (FIGS. 14, 6, 16). Three-dimensional reconstruction of confocal images was performed with ImageJ software. Localization efficiency was calculated by merging Z-stacks into a single image according to average intensity and quantifying fluorescence intensity with ImageJ. Specifically, localization efficiency was calculated as the ratio of fluorescence intensity integrated over microstructured regions to the total fluorescence intensity integrated over the entire region analyzed. Localization efficiencies were reported with standard deviation.

Cell Culture, Staining, and Imaging

PMMA-PCL films with PCL layers 5 μm in thickness were templated with AAO membranes patterned with grooves 10 μm in width and spacing. These films had nanowires approximately 5 μm in length as calculated from the corresponding SEM image shown in FIG. 3, panel A, accounting for the 45° imaging angle. Non-templated PCL, non-patterned nanowire array (fabricated without lithography steps), and micropatterned non-templated PCL (grooves 10 μm in width and 5 μm in height) films were used as controls, with all films incubated in 0.5 M NaOH for 1 h to avoid differences in PCL surface treatment. Prior to cell seeding, the films were rinsed with dH$_2$O 5-10 times and then incubated in a 70% ethanol solution for 5 min. The films were then rinsed in dH$_2$O and allowed to dry under sterile conditions. The films were seeded with NIH/3T3 cells (ATCC, Manassas, Va.) in DMEM (ATCC) medium supplemented with 10% fetal bovine serum and 1× Penicillin-Streptomycin at a density of 5000 cells/cm$^2$. Following two days of cell culture, cells were fixed with 4% paraformaldehyde, permeabilized in 1% Triton X, and blocked in 1% BSA in PBS. The cells were then stained for vinculin with polyclonal anti-vinculin antibodies produced in rabbit (Sigma-Aldrich) diluted 100-fold in 1% BSA in PBS followed by Alexa Fluor® 647 anti-rabbit IgG antibodies produced in goat (Invitrogen) diluted 200-fold in 1% BSA in PBS. The cells were also stained with Alexa Fluor® 488 Phalloidin (Life Technologies) and DAPI (Invitrogen) and mounted for fluorescence imaging. To quantify cellular elongation, at least three separate regions of cells were selected for each sample, and the distance between the two furthest points of each fully visible cell as determined from actin staining was quantified using ImageJ. To quantify cellular alignment (FIG. 19, the angle of the line formed by these points relative to the horizontal axis of the images (which was aligned to microgrooves, if present), was determined using ImageJ, and results were plotted in polar histograms with bins of 30° ranges.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of forming a microdevice comprising a plurality of nanowires on a biocompatible surface, comprising:
    a) depositing onto a surface of a first planar biocompatible polymeric layer a second planar biocompatible polymeric layer, wherein the melting temperature of the first biocompatible polymeric layer is higher than the melting temperature of the second biocompatible polymeric layer;
    b) contacting a surface of the second planar biocompatible polymeric layer with a nanoporous membrane; and
    c) forming the second planar biocompatible polymeric layer into a plurality of nanowires using the nanoporous membrane as a template,
    wherein the nanowires are present on only one surface of the microdevice.

2. The method of claim 1, wherein the forming the second biocompatible polymeric layer into a plurality of nanowires using the nanoporous membrane as a template comprises extruding the second biocompatible polymeric layer through the nanoporous membrane using heat.

3. The method according to claim 1, wherein the method further comprises dissolving the nanoporous membrane after forming the second biocompatible polymeric layer into a plurality of nanowires.

4. The method of claim 3, wherein the dissolving comprises dissolving the nanoporous membrane in an alkaline solution.

5. The method of claim 1, wherein the depositing step a) comprises contacting a heated first biocompatible polymeric layer with the second biocompatible polymeric layer.

6. The method of claim 1, wherein the first planar biocompatible polymeric layer comprises polymethyl methacrylate (PMMA).

7. The method of claim 1, wherein the second biocompatible polymeric layer comprises polycaprolactone (PCL).

8. The method of claim 1, wherein the nanoporous membrane is an anodized metal oxide membrane or a nanoporous silica membrane.

9. The method of claim 8 wherein the anodized metal oxide comprises aluminum, tin or titanium.

10. The method of claim 9 wherein the nanoporous membrane is a nanoporous anodized aluminum oxide (AAO) membrane.

11. The method of claim 1, wherein the method comprises providing the first biocompatible polymeric layer on a substrate prior to step a).

12. The method of claim 11, wherein the method comprises creating a micropattern in the first biocompatible polymeric layer prior to step a).

13. The method of claim 12, wherein creating the micropattern comprises using photolithography.

14. The method of claim 11, wherein the substrate is a silicon wafer.

15. The method of claim 1, wherein the method comprises creating a micropattern in the nanoporous membrane prior to step b).

16. The method of claim 1, wherein the first polymeric layer has an average thickness in the range of 1 to 100 μm.

17. The method of claim 1, wherein the second biocompatible polymeric layer has an average thickness in the range of 1 to 100 μm.

18. The method of claim 1, wherein the average diameter of the pores of the nanoporous membrane is in the range of 10 to 500 nm.

* * * * *